（12） United States Patent
Taki et al.

(10) Patent No.: US 9,352,073 B2
(45) Date of Patent: *May 31, 2016

(54) FUNCTIONAL FILM

(71) Applicant: NIKON CORPORATION, Tokyo (JP)

(72) Inventors: Yusuke Taki, Sagamihara (JP); Tsukasa Kishiume, Sagamihara (JP)

(73) Assignee: NIKO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/856,969

(22) Filed: Sep. 17, 2015

(65) Prior Publication Data
US 2016/0000978 A1    Jan. 7, 2016

Related U.S. Application Data

(60) Continuation-in-part of application No. 14/707,454, filed on May 8, 2015, which is a division of application No. 14/159,871, filed on Jan. 21, 2014, now Pat. No. 9,057,955.

(60) Provisional application No. 61/755,098, filed on Jan. 22, 2013.

(51) Int. Cl.
A61L 31/10    (2006.01)
A61F 2/82    (2013.01)
A61L 31/08    (2006.01)
(Continued)

(52) U.S. Cl.
CPC . *A61L 31/10* (2013.01); *A61F 2/82* (2013.01); *A61L 31/088* (2013.01); *C04B 35/52* (2013.01); *G03F 7/11* (2013.01); *G03F 7/2041* (2013.01); *G03F 7/70341* (2013.01); *A61L 2420/06* (2013.01); *Y10T 428/24322* (2015.01); *Y10T 428/265* (2015.01); *Y10T 428/31678* (2015.04); *Y10T 442/10* (2015.04)

(58) Field of Classification Search
CPC . Y10T 428/30; Y10T 428/265; Y10T 442/10; Y10T 428/31678; Y10T 428/24322; C03C 17/3441; C03C 2217/76; C23C 16/26; C23C 14/0605; C23C 14/548; A61F 2310/00407; A61F 2/82; C04B 41/87; C04B 35/52; G03F 7/11; G03F 7/2041; G03F 7/70341; A61L 31/10; A61L 31/088; A61L 2420/06
USPC ................................. 430/325; 428/457, 336
See application file for complete search history.

(56) References Cited

U.S. PATENT DOCUMENTS 6,208,407 B1    3/2001    Loopstra
6,262,796 B1    7/2001    Loopstra et al.
(Continued)

FOREIGN PATENT DOCUMENTS

EP    2 568 059 A1    3/2013
JP    2005-109426 A    4/2005
(Continued)

OTHER PUBLICATIONS

Mar. 25, 2014 Search Report issued in PCT/JP2014/051234.
(Continued)

*Primary Examiner* — Caleen Sullivan
(74) *Attorney, Agent, or Firm* — Oliff PLC

(57) ABSTRACT

A functional film that is applied to a surface of a medical apparatus or a biomaterial includes a film of Ti-doped tetrahedral amorphous carbon (ta-C:Ti film).

10 Claims, 18 Drawing Sheets

(51) Int. Cl.
*C04B 35/52* (2006.01)
*G03F 7/11* (2006.01)
*G03F 7/20* (2006.01)

(56) References Cited

U.S. PATENT DOCUMENTS

| | | | |
|---|---|---|---|
| 6,341,007 | B1 | 1/2002 | Nishi et al. |
| 6,611,316 | B2 | 8/2003 | Sewell |
| 6,778,257 | B2 | 8/2004 | Bleeker et al. |
| 6,897,963 | B1 | 5/2005 | Taniguchi et al. |
| 9,057,955 | B2 * | 6/2015 | Kishiume ............ G03F 7/2041 |
| 2002/0102398 | A1 | 8/2002 | Shi et al. |
| 2005/0018155 | A1 | 1/2005 | Cox et al. |
| 2005/0280791 | A1 | 12/2005 | Nagasaka et al. |
| 2007/0127006 | A1 | 6/2007 | Shibazaki |
| 2007/0146663 | A1 | 6/2007 | Nagasaka |
| 2008/0018866 | A1 | 1/2008 | Nagasaka et al. |
| 2008/0174748 | A1 | 7/2008 | Nagasaka |
| 2008/0186462 | A1 | 8/2008 | Shima |
| 2008/0266533 | A1 | 10/2008 | Nagasaka et al. |
| 2012/0013864 | A1 | 1/2012 | Sato |
| 2013/0040247 | A1 | 2/2013 | Taki |
| 2013/0058640 | A1 | 3/2013 | Taki |
| 2014/0227644 | A1 | 8/2014 | Kishiume et al. |

FOREIGN PATENT DOCUMENTS

| | | |
|---|---|---|
| JP | 2005-223315 A | 8/2005 |
| JP | 2008-182241 A | 8/2008 |
| WO | 01/35168 A1 | 5/2001 |
| WO | 2004/019128 A2 | 3/2004 |
| WO | 2011/081062 A1 | 7/2011 |
| WO | 2011/138967 A1 | 11/2011 |

OTHER PUBLICATIONS

Mar. 25, 2014 Written Opinion issued in PCT/JP2014/051234.

Amin et al; "Amorphous carbonated apatite formation on diamond-like carbon containing titanium oxide;" Diamond and Related Materials; Mar. 2009; vol. 18; pp. 1139-1144.

Chen et al; "Deposition of titania-containing diamond-like carbon nanocomposite films by sputtering-assisted chemical vapor deposition"; Plasma Processes and Polymers; 2011; vol. 8; pp. 324-332.

Sep. 24, 2014 Office Action issued in U.S. Appl. No. 14/159,871.

Feb. 13, 2015 Notice of Allowance issued in U.S. Appl. No. 14/159,871.

Jun. 2, 2015 Office Action issued in U.S. Appl. No. 14/707,454.

* cited by examiner

○ NEUTRAL PARTICLES
● + IONS

FIG. 5

| Ti CONCENTRATION IN RAW MATERIAL (at%) | | 0.00 | 1.00 | 1.25 | 1.50 | 1.80 | 2.15 | 4.00 |
|---|---|---|---|---|---|---|---|---|
| COMPOSITION OF ta-C:Ti FILM | C (at%) | 100.0 | 97.8 | 96.4 | 95.6 | 93.4 | 84.6 | 82.6 |
| | Ti (at%) | 0.0 | 2.1 | 3.5 | 4.3 | 6.5 | 15.4 | 17.0 |
| | O (at%) | 0.0 | 0.0 | 0.0 | 0.0 | 0.0 | 0.0 | 0.0 |
| | H (at%) | 0.0 | 0.1 | 0.1 | 0.1 | 0.1 | 0.1 | 0.4 |
| Ti/C ATOMIC RATIO | | 0.00 | 0.02 | 0.04 | 0.05 | 0.07 | 0.18 | 0.21 |

FIG. 6

| Ti CONCENTRATION IN RAW MATERIAL (at%) | | 1.50 | 1.50 | 1.50 |
|---|---|---|---|---|
| BIAS VOLTAGE DURING ta-C:Ti FILM FORMATION (V) | | floating | -190 | -1980 |
| COMPOSITION OF ta-C:Ti FILM | sp2-C (at%) | 27.6 | 37.3 | 47.4 |
| | sp3-C (at%) | 67.6 | 58.3 | 48.2 |
| | Ti (at%) | 4.4 | 4.2 | 4.3 |
| | O (at%) | 0.0 | 0.0 | 0.0 |
| | H (at%) | 0.4 | 0.2 | 0.1 |
| Ti/C (sp2-C+sp3-C) ATOMIC RATIO | | 0.046 | 0.044 | 0.045 |

FUNCTIONAL FILM

CROSS-REFERENCE TO RELATED APPLICATION

This is a Continuation-in-Part of application Ser. No. 14/707,454, filed May 8, 2015, which in turn is a Division of application Ser. No. 14/159,871, filed Jan. 21, 2014, which in turn is a non-provisional application claiming priority to and the benefit of U.S. provisional application No. 61/755,098, filed on Jan. 22, 2013. The entire contents of the prior applications are incorporated herein by reference.

BACKGROUND

1. Field of the Invention

The present invention relates to a functional film, a liquid immersion member, a method of manufacturing a liquid immersion member, an exposure apparatus, and a device manufacturing method. More specifically, the present invention relates to a functional film having a surface property with both hydrophilic and antifouling properties, to a liquid immersion member using the functional film, to a method of manufacturing a liquid immersion member, to an exposure apparatus, and to a device manufacturing method.

2. Description of Related Art

In exposure apparatuses used in a photolithography process, a liquid immersion exposure apparatus that exposes a substrate with exposure light through liquid is known, for example, as disclosed in United States Patent Application, Publication No. 2008/266533 and United States Patent Application, Publication No. 2005/018155.

SUMMARY

In liquid immersion exposure apparatuses, components contained in a resist or a topcoat on the surface of a wafer which is a substrate may be eluted into liquid (pure water) in a state where a liquid immersion region is formed on an object such as a substrate. For this reason, there is the possibility of resist or topcoat components eluted into liquid (pure water) being reprecipitated on the surface of a member having the liquid immersion region formed therein, and the precipitates being peeled off by a water flow (liquid flow) and being attached to the substrate. When the substrate is exposed in a state where the precipitates are attached to the substrate, there is the possibility of exposure defects (such as, for example, a pattern defect formed on the substrate) and a defective device. Further, foreign substances mixed into liquid for any reason are attached to the member having the liquid immersion region formed therein, and thus the substrate may be exposed in a state where the attached foreign substances are mixed into the liquid again.

For this reason, it is necessary to periodically clean the member having the liquid immersion region formed therein, and to remove the precipitates on the surface, but an increase in the cleaning time and frequency can lead to productivity deterioration.

In addition, in order to hold liquid immersion water, the surface of the member having the liquid immersion region formed therein is required to have a hydrophilic property. Further, it is required that the surface of the member as unlikely as possible to be contaminated. That is, a surface property with both hydrophilic and antifouling properties is required for the member which is mounted in the exposure apparatus and has the liquid immersion region formed therein. Hitherto, functional films having such surface properties have been not present.

An object of an aspect of the present invention is to provide a functional film having a surface property with both hydrophilic and antifouling properties. In addition, another object of an aspect of the present invention is to provide a liquid immersion member, a method of manufacturing a liquid immersion member, and an exposure apparatus which are capable of reducing the number of exposure defects and reducing deteriorations in productivity. Further, another object of an aspect of the present invention is to provide a device manufacturing method which is capable of reducing the number of defective devices and reducing deteriorations in productivity.

A functional film according to an aspect of the present invention is a functional film which is applied to a surface of a base material used in a state of being immersed in liquid, the functional film including a film of Ti-doped tetrahedral amorphous carbon (ta-C:Ti film).

For example, in the aspect described above, in a composition of the film, a, which is defined by the following Expression (1) and is an atomic ratio of Ti to C (Ti/C atomic ratio), is equal to or greater than 0.03 and equal to or less than 0.09.

[Expression 1]

$$\alpha = \text{(Ti/C atomic ratio)} \quad (1)$$
$$= \text{(number of Ti atoms)}/$$
$$\{\text{(number of } sp^3\text{-C atoms)} + \text{(number of } sp^2\text{-C atoms)}\}$$

here, (number of Ti atoms): number of Ti atoms occupying the film (number of $sp^3$-C atoms): number of carbon atoms having an $sp^3$ hybrid orbital occupying the film (number of $sp^2$-C atoms): number of carbon atoms having an $sp^2$ hybrid orbital occupying the film In the aspect described above, a static contact angle β of pure water at a surface of the film can be equal to or less than 30 degrees.

In the aspect described above, a contamination index γ of a surface of the film which is obtained through comparison with a surface of pure Ti can be equal to or less than 80%.

In the aspect described above, the base material can be formed of Ti.

For example, in the aspect described above, the base material can be formed of Ti, and a proportion δ, which is defined by the following Expression (2), of carbon atoms ($sp^3$-C atoms) having an $sp^3$ hybrid orbital occupying the film can be equal to or less than 59%.

[Expression 2]

$$\delta = \text{(proportion of } sp^3\text{-C atoms)} \quad (2)$$
$$= \text{(number of } sp^3\text{-C atoms)}/$$
$$\{\text{(number of } sp^3\text{-C atoms)} +$$
$$\text{(number of } sp^2\text{-C atoms)} + \text{(number of Ti atoms)}\}$$

here, (number of Ti atoms): number of Ti atoms occupying the film (number of $sp^3$-C atoms): number of carbon atoms having an $sp^3$ hybrid orbital occupying the film.

(number of sp²-C atoms): number of carbon atoms having an sp² hybrid orbital occupying the film A liquid immersion member according to an aspect of the present invention is a liquid immersion member having a liquid immersion space formed therein in a state where liquid is held between an object and the liquid immersion member so that an optical path of exposure light with which the object is irradiated is filled with the liquid, wherein the liquid immersion member is constituted of the base material covered with the functional film according to the aspect described above, and the base material has a mesh shape.

An exposure apparatus according to an aspect of the present invention is an exposure apparatus that exposes a substrate using exposure light through liquid, the exposure apparatus including the liquid immersion member according to the aspect described above.

In the aspect described above, the exposure apparatus can include the liquid immersion member in a portion of a liquid recovery mechanism that recovers liquid.

A device manufacturing method according to an aspect of the present invention includes: a step of exposing a substrate using the exposure apparatus according to the aspect described above; and a step of developing the exposed substrate.

A functional film according to an aspect of the present invention is a functional film which is applied to a surface of a base material, the functional film including a film of Ti-doped tetrahedral amorphous carbon (ta-C:Ti film), wherein in a composition of the film, $\alpha$, which is defined by the following Expression (3) and is an atomic ratio of Ti to C (Ti/C atomic ratio), is equal to or greater than 0.03 and equal to or less than 0.09.

[Expression 3]

$$\alpha = \text{(Ti/C atomic ratio)} \quad (3)$$
$$= \text{(number of Ti atoms)} /$$
$$\{\text{(number of } sp^3\text{-C atoms)} + \text{(number of } sp^2\text{-C atoms)}\}$$

here, (number of Ti atoms): number of Ti atoms occupying the film (number of sp³-C atoms): number of carbon atoms having an sp³ hybrid orbital occupying the film (number of sp²-C atoms): number of carbon atoms having an sp² hybrid orbital occupying the film For example, in the aspect described above, a thickness of the film is equal to or greater than 10 nm and equal to or less than 1 μm.

According to aspects of the present invention, it is possible to provide a functional film having a surface property with both hydrophilic and antifouling properties. In addition, according to aspects of the present invention, it is possible to provide a liquid immersion member, a method of manufacturing a liquid immersion member, and an exposure apparatus which are capable of improving throughput, and reducing the number of exposure defects and reducing deteriorations in productivity. Further, according to aspects of the present invention, it is possible to provide a device manufacturing method which is capable of reducing the number of defective devices and reducing deteriorations in productivity.

BRIEF DESCRIPTION OF THE DRAWINGS

FIG. 5 is a diagram showing chemical compositions of the ta-C:Ti film fabricated using a graphite raw material having various Ti concentrations.

FIG. 6 is a diagram showing relationships between bias voltages and the chemical compositions of the ta-C:Ti film.

DESCRIPTION OF EMBODIMENTS

Hereinafter, embodiments of the present invention will be described with reference to the accompanying drawings, but the present invention is not limited thereto.

<Functional Film>

Figure 1:
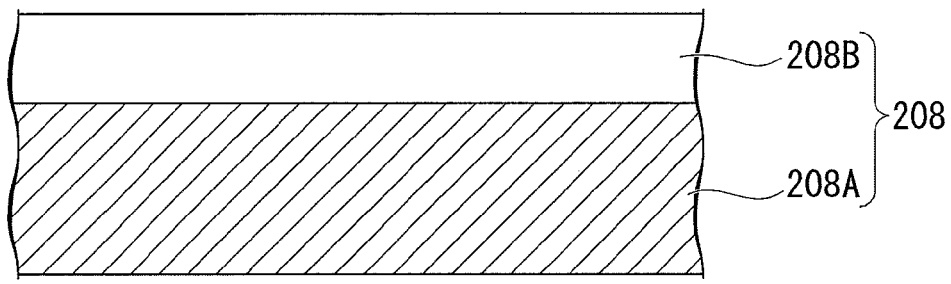
FIG. 1 is a cross-sectional view showing a functional film according to an embodiment of the present invention.

FIG. 1 is a cross-sectional view showing a functional film according to an embodiment of the present invention.

As a result of having repeated assiduous research in order to overcome the above-mentioned problems, the inventors have succeeded in fabricating a functional film with both hydrophilic and antifouling properties by controlling the Ti content of an amorphous carbon film.

As shown in FIG. 1, a functional film 208B according to the embodiment of the present invention is a functional film which is applied to the surface of a base material 208A that is used in a state of being immersed in liquid. The functional film 208B is a Ti-doped tetrahedral amorphous carbon film (hereinafter, referred to as a "ta-C:Ti film"). The material of the base material 208A is not particularly limited, but silicon (Si) or titanium (Ti), for example, can be used. A structure having the functional film 208B disposed on the surface of the base material 208A is also called a sample 208 below.

In the present embodiment, the functional film (ta-C:Ti film) 208B can be formed on at least a portion of a region of the base material 208A which comes into contact with liquid by a filtered cathodic vacuum arc method (FCVA method).

An a-C:Ti film can be fabricated using a CVD method such as a microwave plasma CVD (chemical vapor deposition) method, a direct-current plasma CVD method, a high-frequency plasma CVD method, and an effective magnetic field plasma CVD method, or a PVD method (physical vapor deposition method) such as an ion beam deposition method, an ion beam sputtering method, a magnetron sputtering method, a laser evaporation method, a laser sputtering method, and an arc ion plating method, but the ta-C:Ti film is not likely to be fabricated.

In addition, among the above-mentioned deposition methods, the FCVA method is a deposition method which is capable of performing coating uniformly even on a base material having a complicated shape and with a high adhesion force even at room temperature.

Figure 2A:
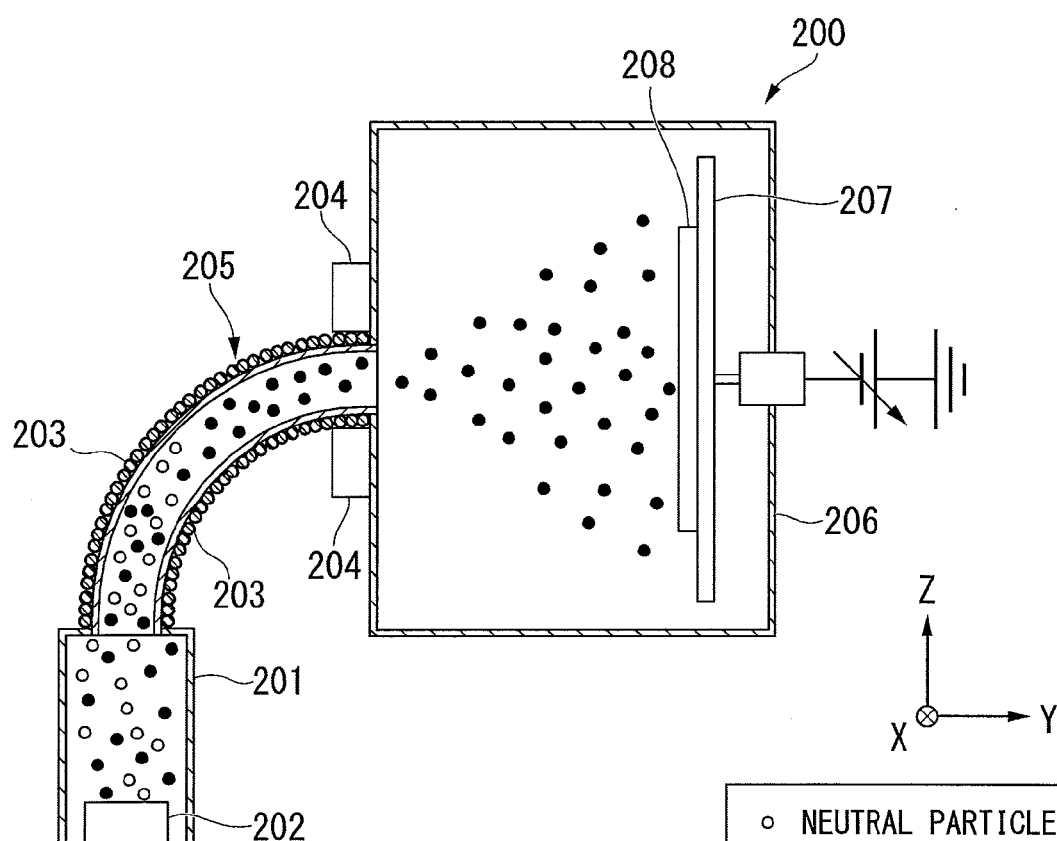
FIG. 2A is a schematic configuration diagram showing an example of an FCVA film formation apparatus.

The FCVA method is a deposition method in which particles ionized by performing arc discharge on a target are generated, and a film is formed by guiding only the particles to a substrate. A schematic configuration diagram of an FCVA apparatus 200 is shown in FIG. 2A. In the FCVA apparatus 200, an arc plasma generation chamber 201 having a graphite target 202 installed therein and a deposition chamber 206 are connected to each other by a space filter 205. The deposition chamber 206 includes a substrate holder 207 therein. The substrate holder 207 fixes the base material 208A, and can incline the base material 208A in a OX direction or rotate the base material in a θY direction by a driving means which is not shown. The space filter 205 is bent double in a −X-axis direction and a Y-axis direction. An electromagnetic coil 203 is wound around the space filter 205, and an ion scan coil 204 is wound in the vicinity of a communication portion with the deposition chamber 206.

In order to form the ta-C:Ti film using the FCVA method, a direct-current voltage is first applied to the graphite target 202 within the arc plasma generation chamber 201, to thereby perform arc discharge and generate arc plasma. Neutral particles, $C^+$ ions, $Ti^+$ ions, $Ti^{2+}$ ions, $Ti^{3+}$ ions, $Ti^{4+}$ ions, and other ions in the generated arc plasma are transported to the space filter 205. In the course of passing through the space filter 205, the neutral particles are trapped by the electromagnetic coil 203, and only the $C^+$ ions, the $Ti^+$ ions, the $Ti^{2+}$ ions, the $Ti^{3+}$ ions, the $Ti^{4+}$ ions, and other ions are guided into the deposition chamber 206. In this case, the flight direction of an ion stream can be changed to any direction by the ion scan coil 204. A negative bias voltage is applied to the base material 208A within the deposition chamber 206. The $C^+$ ions, the $Ti^+$ ions, the $Ti^{2+}$ ions, the $Ti^{3+}$ ions, the $Ti^{4+}$ ions, and other ions which are ionized by the arc discharge are accelerated by the bias voltage, and are deposited on the base material 208A as a dense film.

The ta-C:Ti film formed in this manner is a solid film constituted of C atoms and Ti atoms, and is classified broadly into $sp^2$-C having an $sp^2$ hybrid orbital and $sp^3$-C having an $sp^3$ hybrid orbital with respect to C.

In the FCVA method, the proportion of $sp^3$-C can be controlled by controlling the bias voltage, and the ta-C film and the ta-C:Ti film can be formed. Specifically, in the FCVA method, the content ratio of $sp^2$-C/$sp^3$-C in the ta-C film and the ta-C:Ti film can be controlled by adjusting the bias voltage during film formation. The ta-C:Ti film having a proportion of $sp^3$-C equal to or less than 59% can be formed by adjusting the bias voltage.

On the other hand, the Ti content in the ta-C:Ti film can be controlled by changing the Ti content in a Ti-containing graphite sintered body used as a raw material.

In addition, in the FCVA method, only the $C^+$ ions, the $Ti^+$ ions, the $Ti^{2+}$ ions, the $Ti^{3+}$ ions, the $Ti^{4+}$ ions, and other ions which have substantially the same flight energy are guided into the deposition chamber 206, and ion impact energy of various ion particles incident on the base material 208A can be controlled by controlling the bias voltage which is applied to the base material 208A. Therefore, uniform film formation can be performed even in the base material 208A having a complicated shape.

Regarding the composition of the ta-C:Ti film, when the atomic ratio of Ti to C (Ti/C atomic ratio) is defined as α, α is expressed by the following Expression (1), and α is equal to or greater than 0.03 and equal to or less than 0.09. Thereby, the ta-C:Ti film has a surface property with both hydrophilic and antifouling properties. When α is less than 0.03, the film has an antifouling property, but does not have a sufficient hydrophilic property. On the other hand, when α is greater than 0.09, the film has a super-hydrophilic property, but does not have a sufficient antifouling property.

[Expression 1]

$$\alpha = (\text{Ti/C atomic ratio}) \quad (1)$$
$$= (\text{number of Ti atoms})/$$
$$\{(\text{number of } sp^3\text{-C atoms}) + (\text{number of } sp^2\text{-C atoms})\}$$

Here, (number of Ti atoms): number of Ti atoms occupying the film (number of $sp^3$-C atoms): number of carbon atoms having an $sp^3$ hybrid orbital occupying the film (number of $sp^2$-C atoms): number of carbon atoms having an $sp^2$ hybrid orbital occupying the film When the static contact angle of pure water at the surface of the functional film 208B formed of such a ta-C:Ti film is defined as β, β can be set to be equal to or less than 30 degrees. Thereby, the functional film 208B has a hydrophilic property.

In addition, when the contamination index of the surface of the functional film 208B formed of the ta-C:Ti film which is obtained through comparison with a surface of pure Ti is defined as γ, γ can be set to be equal to or less than 80%. Thereby, the functional film 208B has an antifouling property.

In this manner, the functional film 208B formed of the ta-C:Ti film has a surface property with both hydrophilic and antifouling properties.

In addition, when the base material 208A is formed of titanium (Ti), the proportion δ of carbon atoms ($sp^3$-C atoms) having an $sp^3$ hybrid orbital occupying the functional film which is defined in the following Expression (2) can be set to be equal to or less than 59%. Thereby, the internal stress of the functional film 208B is kept low, and a sufficient adhesion force to the base material 208A can be secured.

[Expression 2]

$$\delta = (\text{proportion of } sp^3\text{-C atoms}) \quad (2)$$
$$= (\text{number of } sp^3\text{-C atoms}) /$$
$$\{(\text{number of } sp^3\text{-C atoms}) +$$
$$(\text{number of } sp^2\text{-C atoms}) + (\text{number of Ti atoms})\}$$

Here, (number of Ti atoms): number of Ti atoms occupying the film (number of $sp^3$-C atoms): number of carbon atoms having an $sp^3$ hybrid orbital occupying the film (number of $sp^2$-C atoms): number of carbon atoms having an $sp^2$ hybrid orbital occupying the film

EXAMPLES

Hereinafter, the present invention will be described more specifically on the basis of examples studied in order to evaluate the characteristics of the functional film according to the embodiment of the present invention, but the present invention is not limited to these examples.

In the present examples, the sample 208 was fabricated by forming the Ti-doped tetrahedral amorphous carbon film (ta-C:Ti film) 208B as a functional film and the pure Ti film as a comparative experiment, on the base material 208A formed of plate-like Si, and the characteristics thereof were evaluated.

Manufacturing Example

The base material 208A was ultrasonically cleaned in an organic solvent, an alkaline solution, and pure water. The base material 208A after cleaning was installed so that film formation was performed on one surface (hereinafter, referred to as the A surface), on a base material holder within the deposition chamber of an FCVA film formation apparatus having a configuration as shown in FIG. 2A. Next, the ta-C:Ti film 208B was formed while inclining the base material holder so that the angle of the A surface of the base material 208A (denoted by "208" in FIGS. 2A to 2C) was set to 45 degrees ($\phi$=45 degrees in FIG. 2B) with respect to the emission direction of a carbon ion beam, and rotating the base material 208A with the substrate holder in such a direction ($\theta$Y direction) that the Y-axis of FIG. 2B was used as a rotational axis, and the sample 208 was obtained.

In this case, graphite sintered bodies containing Ti of 0 at %, 1.0 at %, 1.25 at %, 1.50 at %, 1.8 at %, 2.15 at %, and 4.0 at %, respectively, as targets were used as raw materials. Arc plasma was then generated at an arc current of 80 A for each material and the raw material was evaporated and ionized. The ta-C:Ti film 208B was formed on the base material 208A by setting a bias voltage to 4980 V and applying a pulse of 1500 Hz, and the sample 208 was fabricated. Each film thickness was set to substantially 50 nm by controlling the film formation time. The film thickness was measured by a stylus type step profiler. The film thickness is not limited to 50 nm, but the film thickness between 10 nm and 1,000 nm may be selected. For example, the thickness of the ta-C:Ti film can be set to approximately 10, 20, 30, 40, 50, 60, 70, 80, 90, 100, 200, 300, 400, 500, 600, 700, 800, 900, or 1,000 nm. Meanwhile, a film having a Ti/C atomic ratio of 0 which is fabricated using a pure graphite sintered body raw material having a Ti content of 0 at % is a ta-C film.

The chemical composition of each element in the ta-C:Ti film obtained in this manner was measured. The chemical composition of each element in the ta-C:Ti film was measured by RBS (Rutherford backscattering spectrometry) and HFS (hydrogen forward scattering spectrometry). The results are shown in FIG. 5.

As obvious from FIG. 5, it can be understood that a good-quality Ti-containing tetrahedral amorphous carbon film (ta-C:Ti film) having extremely low concentrations of O and H which are impurities is obtained. As the Ti concentration in the raw material increases, the Ti/C atomic ratio of the ta-C:Ti film also increases.

In addition, a contamination acceleration test was performed on the ta-C film and the ta-C:Ti film having a different Ti/C atomic ratio.

In the contamination acceleration test, the base material 208A formed of plate-like Si was used, and each ta-C:Ti film 208B was formed using a target having a different Ti/C atomic ratio as mentioned above. In addition, the base material 208A formed of pure Ti was also prepared by way of comparison. The sample 208 was vertically immersed in a solution containing a topcoat component as a contamination solution, and was contaminated for 40 hours by a shaker. The results are shown in FIG. 3.

Figure 3:
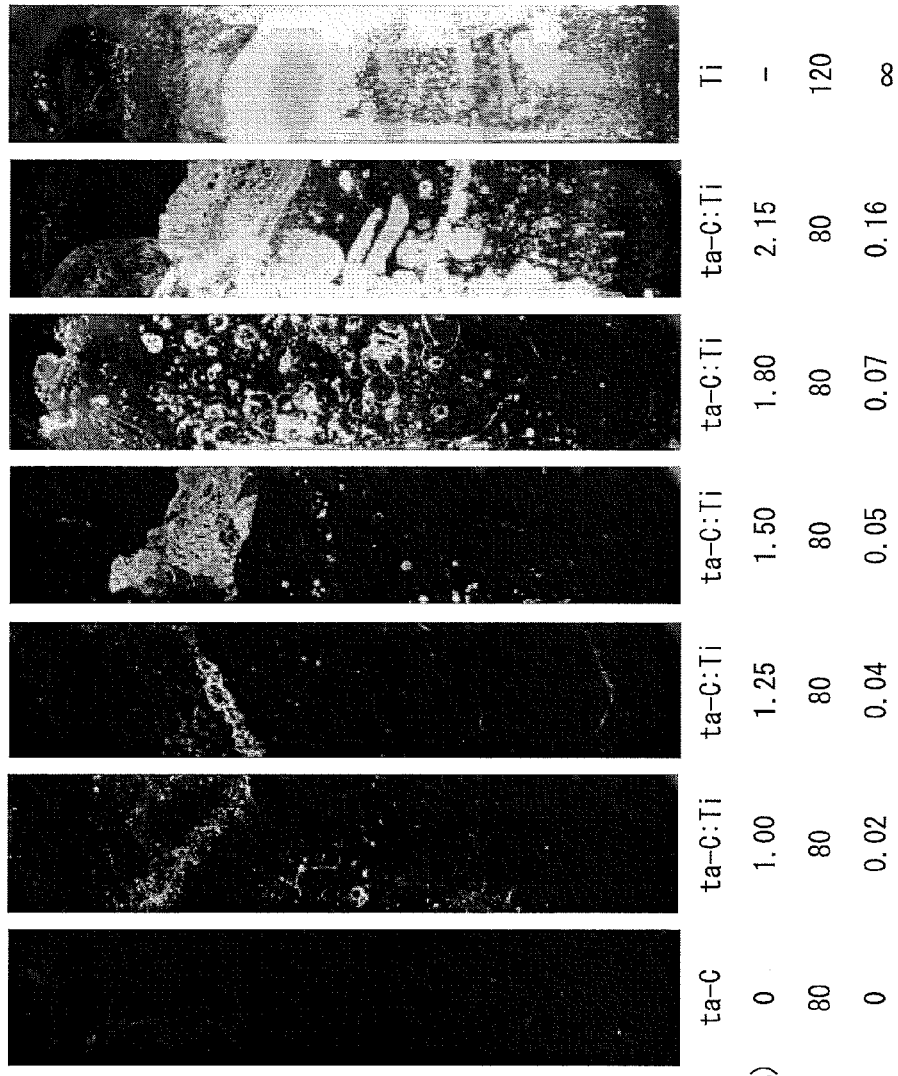
FIG. 3 is an exterior photograph obtained by capturing an image of a film surface of each sample after a contamination acceleration test.

FIG. 3 is an exterior photograph obtained by capturing an image of each sample after the contamination acceleration test from above. Portions appearing to be white are precipitated contaminants formed of a topcoat component.

The ta-C film is almost not contaminated. On the other hand, the pure Ti base material is considerably contaminated. In the ta-C:Ti film, it is clearly known that as the Ti/C atomic ratio increases, the degree of contamination also increases. The area of the white contaminated region was quantified by performing an image process on each photograph of FIG. 3.

Figure 4:
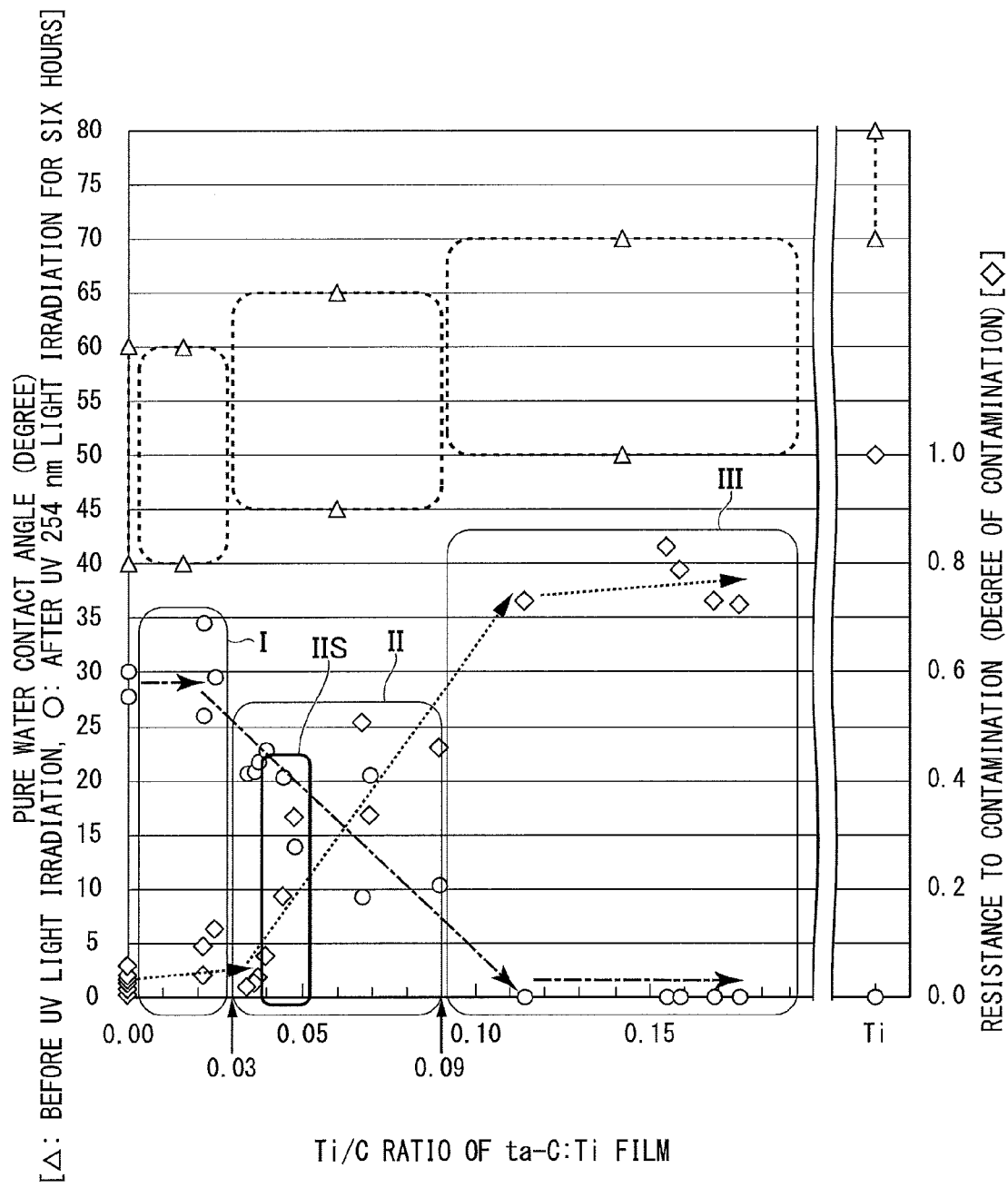
FIG. 4 is a diagram showing results obtained by measuring the quantified degree of contamination and the static contact angle of pure water with respect to a ta-C film and a ta-C:Ti film having various Ti/C atomic ratios.

FIG. 4 is a diagram showing results obtained by measuring the quantified degree of contamination and the static contact angle of pure water with respect to the ta-C film and the ta-C:Ti film having a different Ti/C atomic ratio.

The static contact angle of pure water is indicated by values (▲ marks) measured before irradiation with ultraviolet rays having a wavelength of 254 nm, after the ta-C:Ti film is exposed to the atmosphere before the contamination test is performed, and values (○ marks) measured immediately after the irradiation with ultraviolet rays.

First, a description is given of results obtained by measuring the static contact angle of pure water before the irradiation with ultraviolet rays.

In a case where the Ti/C atomic ratio was 0 (zero: Ti is not contained), that is, in a case of the ta-C film, the static contact angle of pure water was approximately 40 degrees to 60 degrees before the irradiation with ultraviolet rays.

On the other hand, it was found that the static contact angle of pure water of the Ti-doped ta-C:Ti film was approximately 40 degrees to 80 degrees before the irradiation with ultraviolet rays and the water-repellent property was high. In addition, it was also confirmed that as the Ti/C atomic ratio became larger, the contact angle of pure water tended to become larger. Meanwhile, when pure Ti was also evaluated as the comparative example, it was found that in a case of pure Ti, the static contact angle of pure water was 70 degrees to 80 degrees and the water-repellent property was very high.

Next, a description is given of results obtained by measuring the static contact angle of pure water after the irradiation with ultraviolet rays.

When the Ti/C atomic ratio was 0 (zero: Ti is not contained), it was found that the contact angle was remarkably reduced to approximately 28 degrees by the irradiation with ultraviolet rays, as compared to before the irradiation with ultraviolet rays (approximately 40 degrees to 60 degrees).

Similarly to this, it was found that it was possible to reduce the contact angle by the irradiation with ultraviolet rays with respect to the ta-C:Ti film. A detailed description will be provided below.

In a sample of a region I of which the Ti/C atomic ratio (α) was less than 0.03, the contact angle of pure water was approximately 40 degrees to 60 degrees before the irradiation with ultraviolet rays. On the other hand, similarly to a case where Ti was not contained, it was found that the contact angle of pure water was reduced to approximately 28 degrees by the irradiation with ultraviolet rays. In the region I, even when the Ti concentration is changed, great fluctuations in numerical values are not observed.

Next, in a region II of which the Ti/C atomic ratio (α) is equal to or greater than 0.03 and equal to or less than 0.09, it was found that the contact angle of pure water was approximately 45 degrees to 65 degrees before the irradiation with ultraviolet rays, but became less than 28 degrees by the irradiation with ultraviolet rays. In addition, in the region II, it was also found that as the Ti/C atomic ratio (α) increased, the contact angle of pure water decreased drastically.

In addition, in a region III of which the Ti/C atomic ratio (α) was greater than 0.09, it was found that the region had properties resembling those of pure Ti due to the high Ti concentration in the film, the contact angle of pure water was approximately 50 degrees to 70 degrees before the irradiation with ultraviolet rays, but the region was brought into a super-hydrophilic state having a contact angle of substantially 0 (zero) due to the irradiation with ultraviolet rays.

Meanwhile, it was also confirmed that the static contact angle of pure water for pure Ti was 70 degrees to 80 degrees and the water-repellent property was very high before the irradiation with ultraviolet rays, but the region was brought into a super-hydrophilic state having a contact angle of substantially 0 due to the irradiation with ultraviolet rays.

In this manner, in the Ti-doped ta-C:Ti film, it turned out that the contact angle of pure water greatly changed due to the irradiation with ultraviolet rays. That is, the contact angle of pure water decreases drastically, and the film surface has a hydrophilic property. In addition, in the relationship with the Ti/C atomic ratio, it was found that as compared to a tendency before the irradiation with ultraviolet rays (as the Ti/C atomic ratio increases, the contact angle of pure water increases), the tendency after the irradiation with ultraviolet rays showed entirely different behavior.

Next, the degrees of contamination of the ta-C:Ti films of the respective regions I to III were evaluated. The degrees of contamination were relatively quantified (standardized by the area of the contaminated region of pure Ti) by setting the area of the contaminated region of pure Ti to 1. The smaller numerical value represents that the degree of contamination is low. In other words, the smaller numerical value shows that the film is not likely to be contaminated.

From FIG. 4, it can be understood that as the Ti/C atomic ratio (α) increases, the quantified degree of contamination (shown by ◇ marks) tends to become larger, that is, to be easily contaminated.

The region I of which the Ti/C atomic ratio (α) was less than 0.03 had the degree of contamination of less than 0.15, and was not likely to be contaminated. In addition, in the range of the region I, even when the Ti concentration changed, great fluctuations in numerical values were not observed. Next, the region II of which the Ti/C atomic ratio (α) was equal to or greater than 0.03 and equal to or less than 0.09 showed a sharp increase in the degree of contamination as a became larger. In addition, the region III of which the Ti/C atomic ratio (α) was greater than 0.09 had properties resembling those of pure Ti due to the high Ti concentration in the film, had a degree of contamination of equal to or greater than 0.7, and was much more likely to be contaminated. In addition, in the range of the region III, even when the Ti concentration was changed, great fluctuations in numerical values were not seen, but a tendency of saturation was shown.

From the above, regarding the antifouling property of the ta-C:Ti film, the degree of contamination was equal to less than 0.15 in the region I of which α was less than 0.03, and the region was not likely to be contaminated. However, in this region, the contact angle was large, and the hydrophilic property was not sufficient.

On the other hand, regarding the hydrophilic property of the ta-C:Ti film, the region III of which α was greater than 0.09 was brought into a super-hydrophilic state where the contact angle of pure water was 0 (zero). However, the region III had a degree of contamination equal to or greater than 0.7, had the same level as that of pure Ti, and was much more likely to be contaminated.

On the other hand, in the region II in which α was equal to or greater than 0.03 and equal to or less than 0.09, it was found that the contact angle was small, the degree of contamination was also kept low, and both the antifouling property and the hydrophilic property were provided. Particularly, it was found that a sample in a region IIS in which α was equal to or greater than 0.04 and equal or less than 0.05 had an excellent balance of both the antifouling property and the hydrophilic property, and particularly good characteristics were shown.

A property required for the mesh surface of the liquid immersion exposure apparatus may simply be the ability to hold liquid immersion water, and thus a moderate hydrophilic property in which the static contact angle of pure water is less than approximately 30 degrees is good enough without a super-hydrophilic property being required. Preferably, the contact angle is equal to or less than 20 degrees. On the other hand, it is preferable that the antifouling property be higher. In other words, it is preferable that the surface is unlikely to be contaminated. Consequently, it can be concluded that the ta-C:Ti film having the Ti concentration of the region II in FIG. 4 is a ta-C:Ti film having both the antifouling property and the hydrophilic property. Particularly, it was clarified that the ta-C:Ti film having the Ti concentration of the region IIS of which the Ti/C atomic ratio (α) is equal to or greater than 0.04 and equal or less than 0.05 had excellent characteristics.

It can be understood from FIG. 5 that such a ta-C:Ti film serving as the region IIS of which the Ti/C atomic ratio (α) is equal to or greater than 0.04 and equal or less than 0.05 can be fabricated by using a graphite sintered body raw material having a Ti content of 1.25 at % or 1.5 at %.

The $sp^2$-C/$sp^3$-C atomic ratio of the ta-C:Ti film fabricated using the graphite sintered body raw material having a Ti content of 1.5 at % was measured. The atomic ratio of $sp^2$-C atoms to $sp^3$-C atoms was measured by X-ray photoelectron spectroscopy (XPS).

In addition, the ta-C:Ti film was fabricated by changing a bias voltage. The chemical composition of each element of the obtained ta-C:Ti film was measured. The results are shown in FIG. 6.

Meanwhile, the base material 208A formed of Si was used in the sample 208 for chemical composition measurement. The base material 208A formed of Ti was used in the sample 208 for stress measurement.

From FIG. 6, it turned out that it was possible to change the $sp^2$-C/$sp^3$-C atomic ratio by changing the bias voltage.

It can be understood that the proportion (δ) of $sp^3$-C atoms in all the elements constituting the ta-C:Ti film is equal to or less than 59 at %. The value is important. When the $sp^3$-C atomic ratio (δ) exceeds 60 at %, compressive stress is increased, and thus an adhesion force is not able to be secured substantially in various applications. Therefore, in order to secure an adhesion force, the proportion of $sp^3$-C atoms in all the elements constituting the film can be set to be equal to or less than 59 at %. Further, the proportion of $sp^3$-C atoms is preferably equal to or less than 49 at %.

Meanwhile, as the bias voltage, any voltage value between −190 V and −3,000 V may be selected. Thereby, the ta-C:Ti film having low compressive stress is obtained. On the other hand, when any voltage value between floating and −150 V is selected, the ta-C:Ti film having high compressive stress is obtained. In this case, an adhesion force to a Ti mesh becomes weak.

In addition, as understood from FIG. 6, even when the bias voltage is changed, the Ti/C atomic ratio in the ta-C:Ti film remains constant with no change. On the other hand, even when an arc current capable of changing an evaporation rate is changed, the Ti/C atomic ratio (α) in the ta-C:Ti film remains constant with no change. Therefore, the chemical composition and the Ti/C atomic ratio (α) of the ta-C:Ti film can be unmistakably controlled only by the Ti concentration in the raw material.

In the liquid immersion exposure apparatus including the liquid immersion member constituted by a mesh member obtained by forming the film of the region II, a continuous exposure operation was able to be performed while moving a stage at high speed in a state where liquid immersion water was held, and the contamination rate of the liquid immersion member was approximately one-fifth of that of the related art. Therefore, the frequency of stopping the apparatus for the purpose of cleaning and exchanging the liquid immersion member was also one-fifth of that, and thus it was possible to provide a liquid immersion exposure apparatus having much higher throughput than that of an apparatus of the related art.

As described above, the functional film formed of the ta-C:Ti film according to the embodiment of the present invention has both good hydrophilic and antifouling properties.

Such a functional film is used, and thus it is possible to provide a liquid immersion member, a method of manufacturing the liquid immersion member, and an exposure apparatus, which are capable of improving throughput, reducing the number of exposure defects, and reducing deteriorations in productivity. Further, it is possible to provide a device manufacturing method capable of reducing the number of defective devices and reducing deteriorations in productivity.

Hereinafter, the liquid immersion member and the exposure apparatus using the functional film according to the embodiment of the present invention will be described.

Meanwhile, in the following description, an XYZ orthogonal coordinate system is set, and a positional relationship between respective members will be described with reference to the XYZ orthogonal coordinate system. A predetermined direction within the horizontal plane is set to an X-axis direction, a direction orthogonal to the X-axis direction within the horizontal plane is set to a Y-axis direction, and a direction (that is, vertical direction) perpendicular to each of the X-axis direction and the Y-axis direction is set to a Z-axis direction. In addition, rotational (tilting) directions around an X-axis, a Y-axis, and a Z-axis are set to a θX direction, a θY direction, and a θZ direction, respectively. In each embodiment described later, all the base materials of a mesh member 24 (porous member) covered with the functional film are formed of Ti.

First Embodiment

Figure 7:
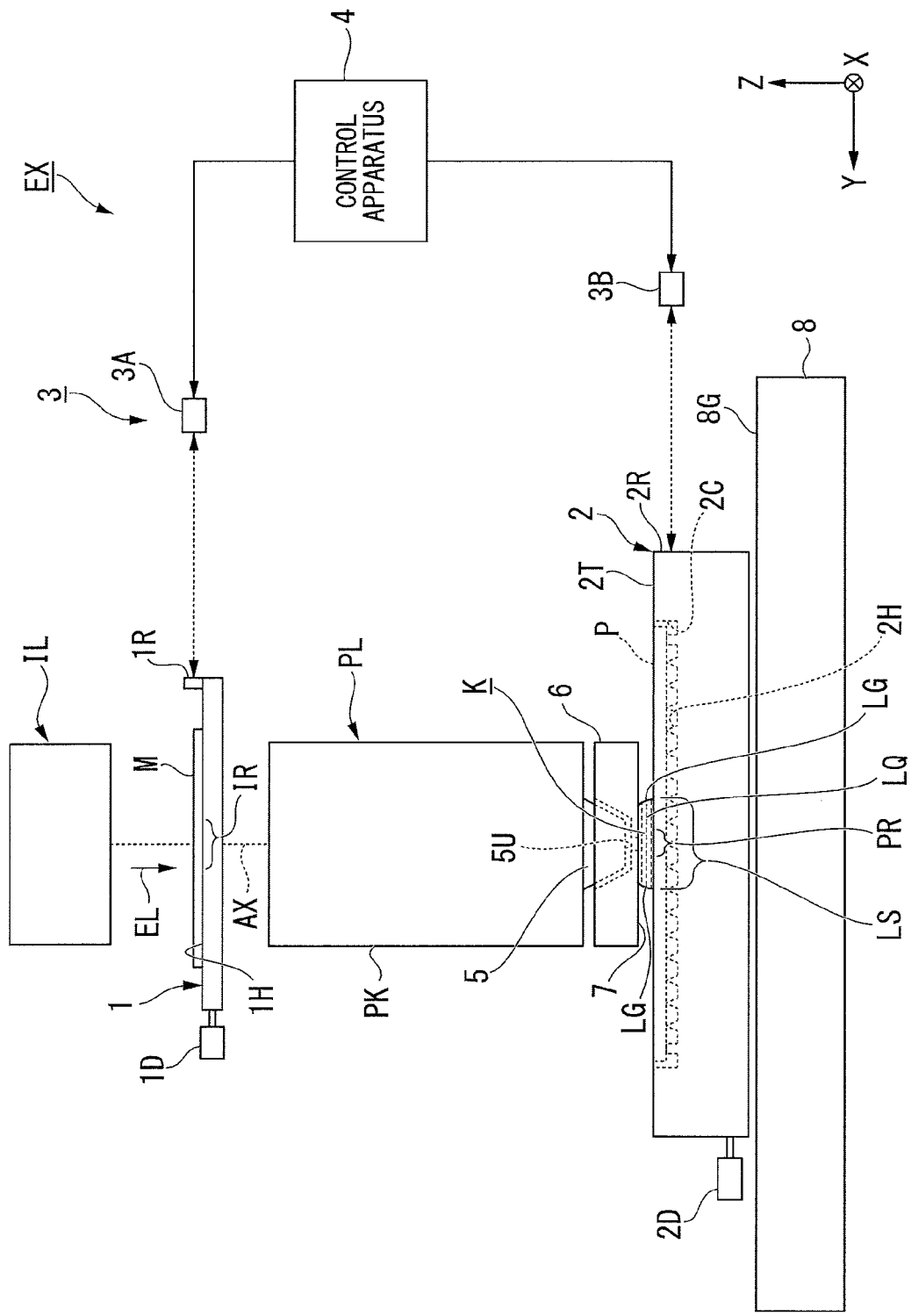
FIG. 7 is a schematic configuration diagram showing an exposure apparatus according to the first embodiment.

A first embodiment will be described below. FIG. 7 is a schematic configuration diagram showing an example of an exposure apparatus EX according to the first embodiment. In FIG. 7, the exposure apparatus EX includes a mask stage 1 that movably holds a mask M, a substrate stage 2 that movably holds a substrate P, a first drive system 1D that moves the mask stage 1, a second drive system 2D that moves the substrate stage 2, an interferometer system 3 capable of measuring positional information of the mask stage 1 and the substrate stage 2, an illumination system IL that illuminates the mask M with exposure light EL, a projection optical system PL that projects an image of a pattern of the mask M, illuminated with the exposure light EL, onto the substrate P, and a control apparatus 4 that controls an operation of the entire exposure apparatus EX.

The mask M includes a reticle on which a device pattern projected onto the substrate P is formed. The mask M includes a transmissive mask having a predetermined pattern formed on a transparent plate such as, for example, a glass plate using a light-shielding film such as chromium. Meanwhile, a reflective mask can also be used as the mask M. The substrate P is a substrate for manufacturing a device. The substrate P includes, for example, a base material such as a semiconductor wafer like a silicon wafer on which a photosensitive film is formed. The photosensitive film is a film formed of a photosensitive material (photoresist). In addition, the substrate P may include a film other than the photosensitive film. For example, the substrate P may include an antireflection film, and may include a protective film (topcoat film) that protects the photosensitive film.

The exposure apparatus EX of the present embodiment is a liquid immersion exposure apparatus that exposes the substrate P with the exposure light EL through liquid LQ. The exposure apparatus EX includes a liquid immersion member 6 capable of forming a liquid immersion space LS so that at least a portion of an optical path K of the exposure light EL is filled with the liquid LQ. The liquid immersion space LS is a space which is filled with the liquid LQ. In the present embodiment, water (pure water) is used as the liquid LQ.

In the present embodiment, the liquid immersion space LS is formed so that the optical path K of the exposure light EL emitted from a terminal optical element 5 which is closest to the image plane of the projection optical system PL among a plurality of optical elements of the projection optical system PL is filled with the liquid LQ. The terminal optical element 5 has an emission surface 5U for emitting the exposure light EL toward the image plane of the projection optical system PL. The liquid immersion space LS is formed so that the optical path K between the terminal optical element 5 and an object disposed at a position facing the emission surface 5U of the terminal optical element 5 is filled with the liquid LQ. The position facing the emission surface 5U includes an irradiation position of the exposure light EL emitted from the emission surface 5U.

The liquid immersion member 6 is disposed in the vicinity of the terminal optical element 5. The liquid immersion member 6 has a lower surface 7. In the present embodiment, the object capable of facing the emission surface 5U can face the lower surface 7. When the surface of the object is disposed at the position facing the emission surface 5U, at least a portion of the lower surface 7 and the surface of the object face each other. When the emission surface 5U and the surface of the object face each other, the liquid LQ can be held between the emission surface 5U and the surface of the object. In addition, when the lower surface 7 of the liquid immersion member 6 and the surface of the object face each other, the liquid LQ can be held between the lower surface 7 and the surface of the object. The liquid immersion space LS is formed by the liquid LQ held between the emission surface 5U and the lower surface 7 on one side and the surface of the object on the other side.

In the present embodiment, the object capable of facing the emission surface 5U and the lower surface 7 includes an object movable on the emission side (image plane side) of the terminal optical element 5, and includes an object movable to the position facing the emission surface 5U and the lower surface 7. In the present embodiment, the object includes at least one of the substrate stage 2 and the substrate P held by the substrate stage 2. Meanwhile, in the following, for the purpose of simplifying description, a state where the emission surface 5U and the lower surface 7 on one side and the surface of the substrate P on the other side face each other will be chiefly described by way of example. However, the same is true of a case where the emission surface 5U and the lower surface 7 on one side and the surface of the substrate stage 2 on the other side face each other.

In the present embodiment, the liquid immersion space LS is formed so that a region (local region) of a portion of the surface of the substrate P disposed at the position facing the emission surface 5U and the lower surface 7 is covered with the liquid LQ, and an interface (a meniscus or an edge) LG of the liquid LQ is formed between the surface of the substrate P and the lower surface 7. That is, in the present embodiment, the exposure apparatus EX adopts a local liquid immersion system in which the liquid immersion space LS is formed so that a portion of a region on the substrate P including a projection region PR of the projection optical system PL is covered with the liquid LQ during the exposure of the substrate P.

The illumination system IL illuminates a predetermined illumination region IR with the exposure light EL having a uniform illuminance distribution. The illumination system IL illuminates at least a portion of the mask M disposed in the illumination region IR with the exposure light EL having a uniform illuminance distribution. As the exposure light EL emitted from the illumination system IL, for example, emission lines (g line, h line, and i line) emitted from a mercury lamp, far-ultraviolet light (DUV light) such as KrF excimer laser light (having a wavelength of 248 nm) and ArF excimer laser light (having a wavelength of 193 nm), vacuum-ultraviolet light (VUV light) such as $F_2$ laser light (having a wavelength of 157 nm), and the like are used. In the present embodiment, as the exposure light EL, ArF excimer laser light which is ultraviolet light (far-ultraviolet light) is used.

The mask stage 1 has a mask holding portion 1H that holds the mask M. The mask holding portion 1H can cause the mask M to be removed therefrom. In the present embodiment, the mask holding portion 1H holds the mask M so that the pattern forming surface (lower surface) of the mask M and the XY plane are substantially parallel to each other. The first drive system 1D includes an actuator such as a linear motor. The mask stage 1 can move within the XY plane by the operation of the first drive system 1D in a state where the mask M is held. In the present embodiment, the mask stage 1 can move in three directions of the X-axis direction, the Y-axis direction, and the θZ direction in a state where the mask M is held by the mask holding portion 1H.

The projection optical system PL irradiates a predetermined projection region PR with the exposure light EL. The projection optical system PL projects an image of a pattern of the mask M, at a predetermined projection magnification, onto at least a portion of the substrate P disposed in the projection region PR. The plurality of optical elements of the projection optical system PL are held by a lens barrel PK. The projection optical system PL of the present embodiment is a reduction system of which the projection magnification is, for example, ¼, ⅕, ⅛ or the like. Meanwhile, the projection optical system PL may be any of an equalization system and a magnification system. In the present embodiment, an optical axis AX of the projection optical system PL is substantially parallel to the Z-axis. In addition, the projection optical system PL may be any of a refraction system which does not include a reflective optical element, a reflection system which does not include a refractive optical element, and a reflection and refraction system which includes a reflective optical element and a refractive optical element. In addition, the projection optical system PL may form any of an inverted image and an erected image.

The substrate stage 2 can move on a guide surface 8G of a base member 8. In the present embodiment, the guide surface 8G is substantially parallel to the XY plane. The substrate stage 2 can move within the XY plane along the guide surface 8G in a state where the substrate P is held.

The substrate stage 2 has a substrate holding portion 2H that holds the substrate P. The substrate holding portion 2H can releasably hold the substrate P. In the present embodiment, the substrate holding portion 2H holds the substrate P so that the exposure surface (surface) of the substrate P and the XY plane are substantially parallel to each other. The second drive system 2D includes an actuator such as a linear motor. The substrate stage 2 can move within the XY plane by the operation of the second drive system 2D in a state where the substrate P is held. In the present embodiment, the substrate stage 2 can move in six directions of the X-axis direction, the Y-axis direction, the Z-axis direction, the θX direction, the θY direction, and the θZ direction in a state where the substrate P is held by the substrate holding portion 2H.

The substrate stage 2 has an upper surface 2T disposed in the vicinity of the substrate holding portion 2H. In the present embodiment, the upper surface 2T is flat, and is substantially parallel to the XY plane. In addition, the substrate stage 2 has a concave portion 2C. The substrate holding portion 2H is disposed inside the concave portion 2C. In the present embodiment, the upper surface 2T and the surface of the substrate P held by the substrate holding portion 2H are disposed in substantially the same plane (are flush with each other).

The interferometer system 3 measures positional information of the mask stage 1 and the substrate stage 2 in the XY plane. The interferometer system 3 includes a laser interferometer 3A that measures the positional information of the mask stage 1 in the XY plane and a laser interferometer 3B that measures the positional information of the substrate stage 2 in the XY plane. The laser interferometer 3A irradiates a reflective surface 1R disposed on the mask stage 1 with measurement light, and measures the positional information of the mask stage 1 (mask M) regarding the X-axis direction, the Y-axis direction, and the θZ direction, using the measurement light through the reflective surface 1R. The laser interferometer 3B irradiates a reflective surface 2R disposed on the substrate stage 2 with measurement light, and measures the positional information of the substrate stage 2 (substrate P) regarding the X-axis direction, the Y-axis direction, and the θZ direction, using the measurement light through the reflective surface 2R.

In addition, in the present embodiment, a focusing and leveling detection system (not shown in the drawing) that detects positional information of the surface of the substrate P held by the substrate stage 2 is disposed. The focusing and leveling detection system detects the positional information of the surface of the substrate P regarding the Z-axis direction, the OX direction, and the θY direction.

When the substrate P is exposed, the positional information of the mask stage 1 is measured by the laser interferometer 3A, and the positional information of the substrate stage 2 is measured by the laser interferometer 3B. The control apparatus 4 brings the first drive system 1D into operation on the basis of the measurement result of the laser interferometer 3A, and executes position control of the mask M held by the mask stage 1. In addition, the control apparatus 4 brings the second drive system 2D into operation on the basis of the measurement result of the laser interferometer 3B and the detection result of the focusing and leveling detection system, and executes position control of the substrate P held by the substrate stage 2.

The exposure apparatus EX of the present embodiment is a scanning-type exposure apparatus (so-called scanning stepper) that projects an image of the pattern of the mask M onto the substrate P while synchronously moving the mask M and the substrate P in a predetermined scanning direction. When the substrate P is exposed, the control apparatus 4 controls the mask stage 1 and the substrate stage 2, and moves the mask M and the substrate P in a predetermined scanning direction within the XY plane intersecting the optical path (optical axis AX) of the exposure light EL. In the present embodiment, the scanning direction (synchronous movement direction) of the substrate P is set to the Y-axis direction, and the scanning direction (synchronous movement direction) of the mask M is also set to the Y-axis direction. The control apparatus 4 moves the substrate P in the Y-axis direction with respect to the projection region PR of the projection optical system PL, and moves the mask M in the Y-axis direction with respect to the illumination region IR of the illumination system IL in synchronization with the movement of the substrate P in the Y-axis direction, while irradiating the substrate P with the exposure light EL through the projection optical system PL and the liquid LQ of the liquid immersion space LS on the substrate P. Thereby, the substrate P is exposed with the exposure light EL, and the image of the pattern of the mask M is projected onto the substrate P.

Figure 8:
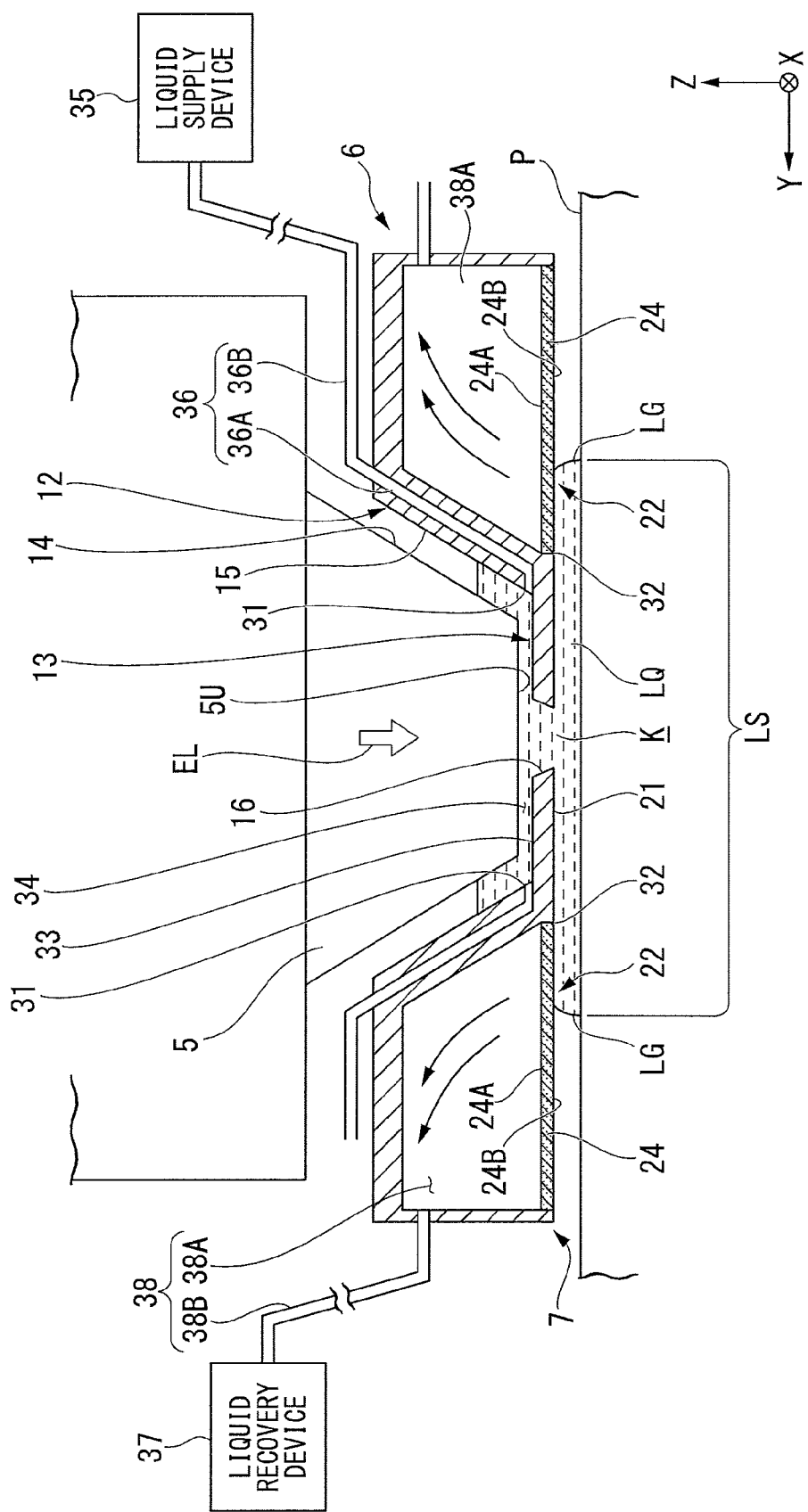
FIG. 8 is a cross-sectional side view showing the vicinity of the liquid immersion member according to the first embodiment.

Next, an example of the liquid immersion member 6 according to the present embodiment and a method of manufacturing the liquid immersion member 6 will be described with reference to the accompanying drawings. FIG. 8 is a cross-sectional side view showing the vicinity of the liquid immersion member 6.

Meanwhile, in the following description, a case where the surface of the substrate P is disposed at the position facing the emission surface 5U of the terminal optical element 5 and the lower surface 7 of the liquid immersion member 6 is described by way of example. However, as described above, objects, such as the upper surface 2T of the substrate stage 2, other than the substrate P can also be disposed at the position facing the emission surface 5U of the terminal optical element 5 and the lower surface 7 of the liquid immersion member 6. In addition, in the following description, the emission surface 5U of the terminal optical element 5 may be referred to as the lower surface 5U of the terminal optical element 5.

The liquid immersion member 6 can form the liquid immersion space LS so that the optical path K of the exposure light EL between the terminal optical element 5 and the substrate P is filled with the liquid LQ. The liquid immersion member 6 is an annular member, and is disposed so as to surround the optical path K of the exposure light EL. In the present embodiment, the liquid immersion member 6 includes a side plate portion 12 disposed in the vicinity of the terminal optical element 5, and a lower plate portion 13 of which at least a portion is disposed between the lower surface 5U of the terminal optical element 5 and the surface of the substrate P, in the Z-axis direction.

Meanwhile, the liquid immersion member 6 may be not an annular member. For example, the liquid immersion member 6 may be disposed in a portion of the vicinity of the optical path K of the exposure light EL emitted from the terminal optical element 5 and the emission surface 5U.

The side plate portion 12 faces an outer circumferential surface 14 of the terminal optical element 5, and a predetermined gap is formed between the side plate portion and an inner circumferential surface 15 which is formed along the outer circumferential surface.

The lower plate portion 13 has an opening 16 in the center thereof. The exposure light EL emitted from the lower surface 5U can pass through the opening 16. For example, the exposure light EL emitted from the lower surface 5U during the exposure of the substrate P passes through the opening 16, and the surface of the substrate P is irradiated with the exposure light through the liquid LQ. In the present embodiment, the exposure light EL in the opening 16 is long and rectangular (slit-shaped) in cross-sectional shape in the X-axis direction. The opening 16 has a shape according to the cross-sectional shape of the exposure light EL. That is, the opening 16 in the XY plane is rectangular (slit-shaped) in shape. In addition, the cross-sectional shape of the exposure light EL in the opening 16 and the shape of the projection region PR of the projection optical system PL in the substrate P are substantially the same as each other.

In addition, the liquid immersion member 6 includes a supply port 31 that supplies the liquid LQ used to form the liquid immersion space LS, and a recovery port 32 that suctions and recovers at least a portion of the liquid LQ on the substrate P.

In the present embodiment, the lower plate portion 13 of the liquid immersion member 6 is disposed in the vicinity of the optical path of the exposure light EL. An upper surface 33 of the lower plate portion 13 is directed toward the +Z-axis direction, and the upper surface 33 and the lower surface 5U face each other with a predetermined gap interposed therebetween. The supply port 31 can supply the liquid LQ to an internal space 34 between the lower surface 5U and the upper surface 33. In the present embodiment, the supply port 31 is provided on each of both sides in the Y-axis direction with respect to the optical path K.

The supply port 31 is connected to a liquid supply device 35 through a channel 36. The liquid supply device 35 can send out the liquid LQ which is cleaned and temperature-regulated. The channel 36 includes a supply channel 36A formed inside the liquid immersion member 6, and a channel 36B formed by a supply tube that connects the supply channel 36A to the liquid supply device 35. The liquid LQ sent out from the liquid supply device 35 is supplied to the supply port 31 through the channel 36. The supply port 31 supplies the liquid LQ from the liquid supply device 35 to the optical path K.

The recovery port 32 is connected to a liquid recovery device 37 through a channel 38. The liquid recovery device 37 includes a vacuum system, and can suction and recover the liquid LQ. The channel 38 includes a recovery channel 38A formed inside the liquid immersion member 6, and a channel 38B formed by a recovery tube that connects the recovery channel 38A to the liquid recovery device 37. By the liquid recovery device 37 being operated, the liquid LQ recovered from the recovery port 32 is recovered to the liquid recovery device 37 through the channel 38.

In the present embodiment, the mesh member 24 (porous member) is disposed in the recovery port 32 of the liquid immersion member 6. At least a portion of the liquid LQ between the substrate P and the mesh member is recovered through the recovery port 32 (mesh member 24). The lower surface 7 of the liquid immersion member 6 includes a land surface 21 disposed in the vicinity of the optical path K of the exposure light EL, and a liquid recovery region 22 provided outside the land surface 21 with respect to the optical path K of the exposure light EL. In the present embodiment, the liquid recovery region 22 includes the surface (lower surface) of the mesh member 24.

In the following description, the liquid recovery region 22 may be referred to as the recovery surface 22.

The land surface 21 can hold the liquid LQ between the surface of the substrate P and the land surface. In the present embodiment, the land surface 21 is directed toward the −Z-axis direction, and includes the lower surface of the lower plate portion 13. The land surface 21 is disposed in the vicinity of the opening 16. In the present embodiment, the land surface 21 is flat, and is substantially parallel to the surface (XY plane) of the substrate P. In the present embodiment, the land surface 21 in the XY plane is rectangular in outer shape, but may have other shapes, for example, a circular shape.

The recovery surface 22 can recover at least a portion of the liquid LQ between the lower surface 5U and the lower surface 7 on one side and the surface of the substrate P on the other side. The recovery surface 22 is disposed on each of both sides in the Y-axis direction (scanning direction) with respect to the optical path K of the exposure light EL. In the present embodiment, the recovery surface 22 is disposed in the vicinity of the optical path K of the exposure light EL. That is, the recovery surface 22 is disposed in an annular rectangular shape in the vicinity of the land surface 21. In addition, in the present embodiment, the land surface 21 and the recovery surface 22 are disposed in substantially the same plane (are flush with each other). Meanwhile, the land surface 21 and the recovery surface may not be disposed in the same plane.

The recovery surface 22 includes the surface (lower surface) of the mesh member 24, and recovers the liquid LQ which is in contact with the recovery surface 22 through holes of the mesh member 24.

Figure 9A:
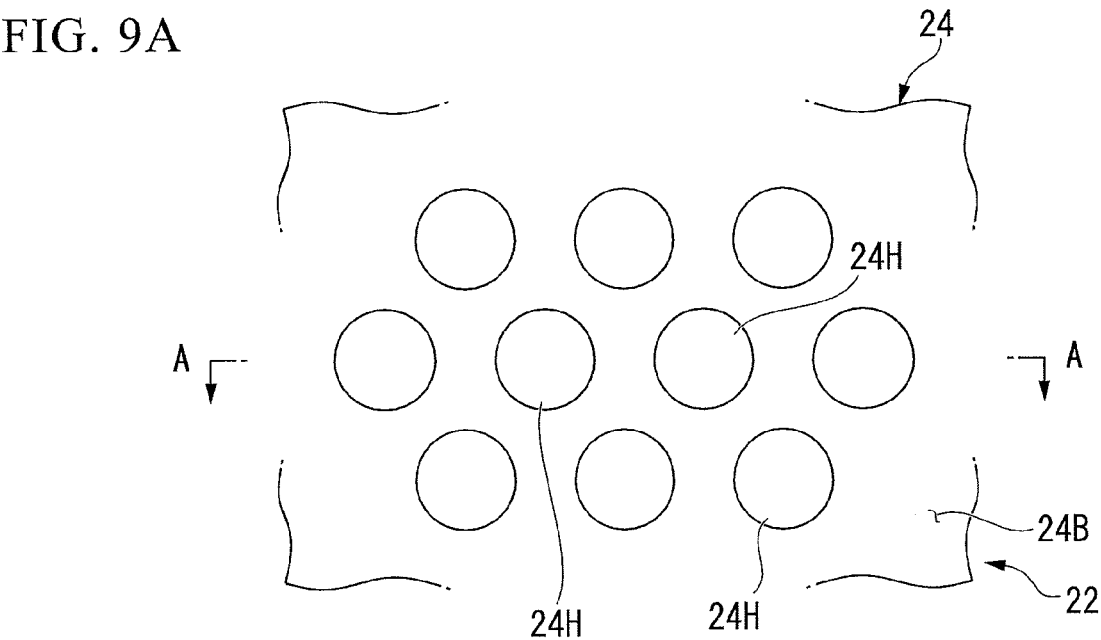
FIG. 9A is a diagram showing an example of a mesh member according to the first embodiment.
Figure 9B:
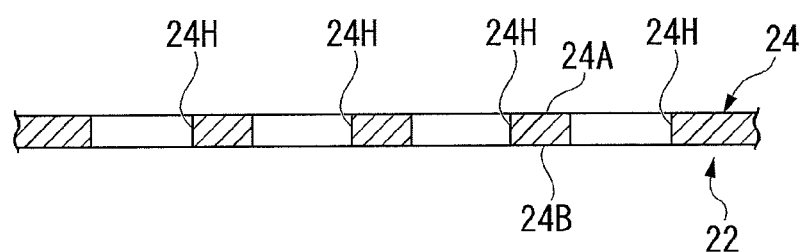
FIG. 9B is a diagram showing an example of the mesh member according to the first embodiment.

FIG. 9A is an enlarged plan view showing the mesh member 24 of the present embodiment, and FIG. 9B is a cross-sectional view taken along an arrow of line A-A in FIG. 9A. As shown in FIGS. 9A and 9B, in the present embodiment, the mesh member 24 is a thin plate member in which a plurality of small holes 24H are formed. The mesh member 24 is a member in which the plurality of holes 24H are formed by processing a thin plate member, and is also called a mesh plate.

The mesh member 24 has a lower surface 24B facing the surface of the substrate P, and an upper surface 24A located on the opposite side to the lower surface 24B. The lower surface 24B has the recovery surface 22 formed thereon. The upper surface 24A comes into contact with the recovery channel 38A. The holes 24H are formed between the upper surface 24A and the lower surface 24B. That is, the holes 24H are formed so as to penetrate through the upper surface 24A and the lower surface 24B. In the following description, the hole 24H may be referred to as the through-hole 24H.

In the present embodiment, the upper surface 24A and the lower surface 24B are substantially parallel to each other. That is, in the present embodiment, the upper surface 24A and the lower surface 24B are substantially parallel to the surface of the substrate P (XY plane). In the present embodiment, the through-hole 24H penetrates between the upper surface 24A and the lower surface 24B in substantially parallel to the Z-axis direction. The liquid LQ can flow through the through-hole 2414. The liquid LQ on the substrate P is drawn into the recovery channel 38A through the through-hole 24H.

In the present embodiment, the through-hole (opening) 24H in the XY plane is circular in shape. In addition, the size of the through-hole (opening) 24H in the upper surface 24A and the size of the through-hole (opening) 24H in the lower surface 24B are substantially equal to each other. Meanwhile, the shape of the through-hole 24H in the XY plane may be shapes other than a circular shape, for example, polygonal shapes such as a pentagonal shape and a hexagonal shape. In addition, the diameter or shape of the through-hole (opening) 24H in the upper surface 24A may be different from the diameter or shape of the through-hole (opening) 24H in the lower surface 24B.

In the present embodiment, the control apparatus 4 brings the liquid recovery device 37 including the vacuum system into operation, and generates a pressure difference between the upper surface 24A and the lower surface 24B of the mesh member 24, to thereby recover the liquid LQ from the mesh member 24 (recovery surface 22). The liquid LQ recovered from the recovery surface 22 is recovered to the liquid recovery device 37 through the channel 38.

There is the possibility of substances (for example, organic substances such as a resist and a topcoat) eluted from the substrate P into the liquid LQ, during the exposure of the substrate P, being reprecipitated on the surface of the member constituting the liquid immersion member 6. When precipitates are generated in a region which is in contact with the liquid LQ of the liquid immersion member 6, there is the possibility of the precipitates being peeled off by a liquid flow (water flow) and being attached to the substrate P.

In the present embodiment, the functional film as described above, that is, the Ti-doped tetrahedral amorphous carbon film (ta-C:Ti film) is formed in at least a portion of the region which is in contact with the liquid LQ of the liquid immersion member 6. The ta-C:Ti film is chemically inactive, and has a property excellent in an adhesion force to a ground (base material) on which the film is to be formed. In addition, the ta-C:Ti film of the present embodiment has both a hydrophilic property and an antifouling property.

For this reason, in the present embodiment, in a region of the liquid immersion member 6 where the ta-C:Ti film is formed, even when a chemical affinity with a resist component or a topcoat component eluted into the adjoining liquid LQ is low, and the wetting and drying of the liquid LQ are repeated, the adhesion and reprecipitation of the resist component or the topcoat component in the liquid LQ are not likely to occur. Therefore, it is possible to effectively reduce the number of exposure defects due to the reprecipitation of the topcoat component on the surface of the liquid immersion member 6 in the region which is in contact with the liquid LQ, the peeling-off of the reprecipitates, and the attachment thereof to the surface of the substrate P during exposure. It is thereby possible to improve throughput.

In the present embodiment, a portion having the ta-C:Ti film formed on the surface of the liquid immersion member 6 is not particularly limited as long as it is a region which comes into contact with the liquid LQ. The portion may have only to be formed on at least a portion of a region which comes into contact with the liquid LQ of the liquid recovery region 22 (recovery port 32 and mesh member 24), the land surface 21, the lower plate portion 13, and the side plate portion 12. The ta-C:Ti film can be configured to be formed in a region in which the reprecipitation of the resist component or the topcoat component has a tendency to occur, and a region which has a tendency to be influenced by the liquid flow of the liquid LQ, among these members constituting the liquid immersion member 6.

With such a configuration, it is possible to suppress the reprecipitation of the resist component or the topcoat component, and to suppress the peeling-off of the reprecipitates and the adhesion thereof to the substrate P. The region in which the reprecipitation of the resist component or the topcoat component has a tendency to occur and the region which has a tendency to be influenced by the liquid flow of the liquid LQ include particularly the recovery port 32 (mesh member 24) of the liquid recovery region 22. The ta-C:Ti film is formed on the surface of the recovery port 32 (mesh member 24), and thus it is possible to effectively suppress the reprecipitation of the resist component or the topcoat component, the peeling-off of the reprecipitates, and the adhesion of the reprecipitates to the substrate P, and to reduce the number of exposure defects.

In addition, according to the present embodiment, since the reprecipitation of the resist component or the topcoat component on the liquid immersion member 6 is not likely to occur, it is possible to reduce the frequency of cleaning of the liquid immersion member 6. In addition, the ta-C:Ti film is formed on the surface of the liquid immersion member 6. Thereby, even when the reprecipitation of the resist component or the topcoat component is caused by a repeated exposure process, a low chemical affinity between the surface of the liquid immersion member 6 and the resist component or the topcoat component gives rise to a weak adhesion force therebetween, and thus it is possible to shorten the cleaning time of the reprecipitates. Therefore, according to the present embodiment, since the frequency and time of the cleaning work can be reduced, it is possible to shorten the downtime of the liquid immersion exposure apparatus, and to reduce deteriorations in productivity.

In the present embodiment, the base material of the liquid immersion member 6 is made of Ti. Thereby, the internal stress of the ta-C:Ti film is kept low, and thus it is possible to secure a sufficient adhesion force to the base material of the liquid immersion member 6. Meanwhile, the base material of the liquid immersion member 6 may be corrosive-resistant metal products or ceramic products made of stainless steel, Al or the like.

The thickness of the ta-C:Ti film formed in at least a portion of the liquid immersion member 6 is not particularly limited, but can be set to be equal to or greater than 5 nm, and is preferably 10 nm to 1 μm. As the ta-C:Ti film, a film having hydrogen scarcely contained therein can be used.

Figure 9C:
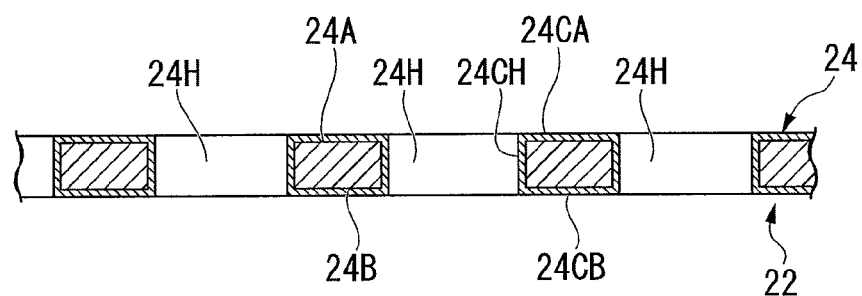
FIG. 9C is a diagram showing an example of the mesh member according to the first embodiment.

FIG. 9C is a cross-sectional view taken along an arrow showing an example when the ta-C:Ti film is formed in the mesh member 24 of the recovery port 32 in the present embodiment.

In the present embodiment, as shown in FIG. 9C, the ta-C:Ti film is formed on the lower surface 24B, the inner wall surface of the through-hole 24H, and the upper surface 24A. The thicknesses of the ta-C:Ti film on the lower surface 24B, the inner wall surface of the through-hole 24H, and the upper surface 24A are not particularly limited. A continuous ta-C:Ti film may be formed without being formed in an island shape in order to obtain an effect obtained by forming a chemically inactive ta-C:Ti film, and the thicknesses thereof can be set to be equal to or greater than 5 nm, preferably 10 nm to 1 μm. For example, the thicknesses of the ta-C:Ti film can be set to approximately 10, 20, 30, 40, 50, 60, 70, 80, 90, 100, 200, 300, 400, 500, 600, 700, 800, 900, or 1,000 nm. The thicknesses of the ta-C:Ti film formed on the lower surface 24B, the upper surface 24A, and the inner wall surface of the through-hole 24H may be substantially the same as or different from each other. The thickness of the ta-C:Ti film on the inner wall surface of the through-hole 24H can be adjusted by the hole diameter of the through-hole 24H. Meanwhile, the ta-C:Ti film may be formed on only the lower surface 24B and/or the upper surface 24A.

In the present embodiment, as shown in FIG. 9C, when the ta-C:Ti film is formed in the mesh member 24 of the recovery port 32, the film formation can be performed using an FCVA method which is capable of performing uniform film formation even on the inner wall surface of the fine through-hole 24H.

As shown in FIG. 9C, a description will be given of a method of forming the ta-C:Ti film on the upper surface 24A, the lower surface 24B, and the inner wall surface of the through-hole 24H of the mesh member 24 using an FCVA method.

Figure 2B:
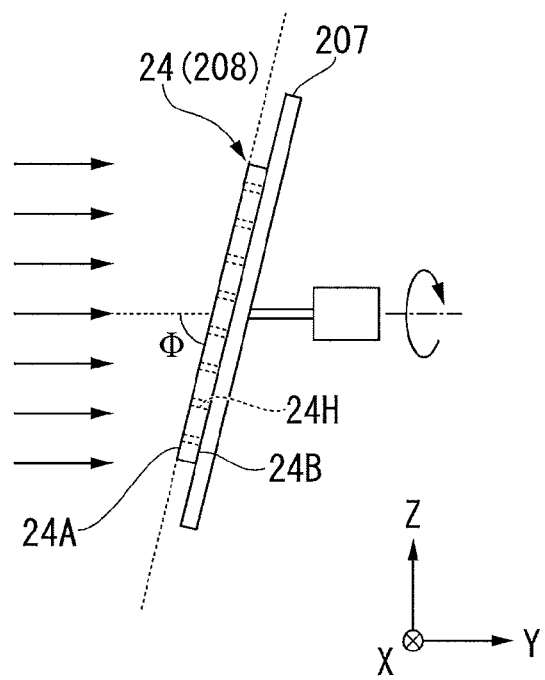
FIG. 2B is a diagram showing a method of manufacturing a liquid immersion member according to a first embodiment.
Figure 2C:
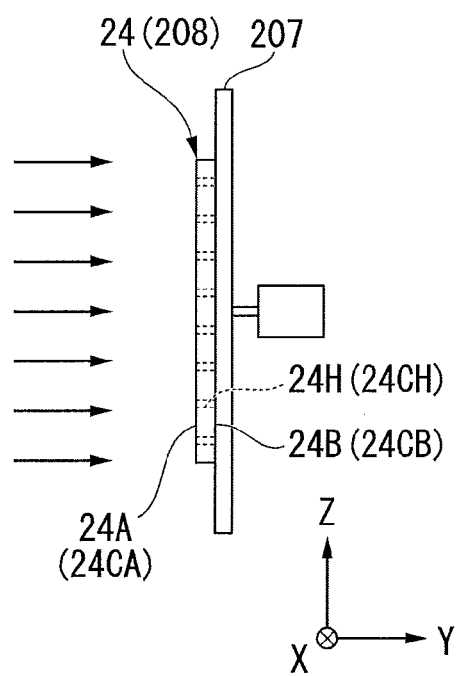
FIG. 2C is a diagram showing a method of manufacturing the liquid immersion member according to the first embodiment.

First, in the FCVA apparatus 200 shown in FIG. 2A, the mesh member 24 is installed on the substrate holder 207 so that the upper surface 24A of the mesh member 24 faces the flight direction (Y-axis direction) of $C^+$ ion particles. Next, as shown in FIG. 2B, by operating the substrate holder 207 through driving means which is not shown in the drawing, the mesh member 24 is rotated in the θX direction, and is inclined so that the plane of the upper surface 24A is set to have an angle Φ with respect to the Y-axis which is the flight direction of $C^+$ ions. Further, the ta-C:Ti film is formed while rotating the mesh member in the θY direction through driving means (not shown in the drawing) of the substrate holder 207. By installing and rotating the mesh member 24 in such a manner and performing film formation, the $C^+$ ions reach not only the upper surface 24A of the mesh member 24, but also the inner wall surface of the through-hole 24H, thereby allowing the ta-C:Ti film to be formed. Meanwhile, the tilt angle Φ of the plane of the upper surface 24A of the mesh member 24 with respect to the Y-axis (flight direction of $C^+$ ions) is not particularly limited as long as it is an angle at which the $C^+$ ions reach the inside of the through-hole 24H of the mesh member 24 and the ta-C:Ti film can be formed on the inner wall surface of the through-hole 24H. For example, the tilt angle can be set to 45 degrees.

After the ta-C:Ti film is formed on the upper surface 24A side of the mesh member 24, the mesh member 24 is removed from the substrate holder 207, and the mesh member 24 having one surface (upper surface 24A) on which the film is formed is installed on the substrate holder 207 so that the lower surface 24B faces the flight direction (Y-axis direction) of $C^+$ ion particles. Next, the ta-C:Ti film is formed on the lower surface 24B side of the mesh member 24 in the same procedure as that of the aforementioned film formation method of the upper surface 24A side while rotating the mesh member at the tilt angle Φ in the θY direction. The tilt angle Φ of the plane of the lower surface 24B with respect to the Y-axis when the ta-C:Ti film is formed on the lower surface 24B side of the mesh member 24 can be set to the same as the tilt angle Φ of the plane of the lower surface 24A with respect to the Y-axis when film formation is performed on the upper surface 24A side. By installing the mesh member 24 and performing film formation so that the tilt angle Φ during the film formation on the upper surface 24A side and the tilt angle Φ during the film formation of the lower surface 24B side are the same as each other, it is possible to achieve the uniformity of the thickness of the ta-C:Ti film formed on the inner wall surface of the through-hole 24H. The ta-C:Ti film is formed on the upper surface 24A, the lower surface 24B, and the inner wall surface of the through-hole 24H of the mesh member 24 using the above-mentioned method, and thus it is possible to manufacture the liquid immersion member 6 according to the present embodiment.

In the liquid immersion member 6 of the present embodiment, a region having a ta-C:Ti film formed on the surface thereof has a liquid-repellent property, but at least a portion of the ta-C:Ti film can be set to have a lyophilic property in order to hold the liquid LQ to form the liquid immersion space LS, and supply and recover the liquid LQ smoothly. Meanwhile, in the present embodiment, the term "liquid-repellent property" indicates that a contact angle when pure water is dropped on the surface exceeds 50 degrees, and the term "lyophilic property" indicates that a contact angle when pure water is dropped on the surface is equal to or less than 50 degrees.

The change of the region having the ta-C:Ti film of the liquid immersion member 6 formed therein from a liquid-repellent property to a lyophilic property can be performed by irradiating a region desired to be set to have a lyophilic property in the region having the ta-C:Ti film formed therein, with ultraviolet rays in the atmosphere. When the ta-C:Ti film is set to have a hydrophilic property, ultraviolet rays having a wavelength of 254 nm can be used.

In addition, the hydrophilic property may deteriorate due to contaminants (resist component or topcoat component) attached to the surface of the ta-C:Ti film, but the lyophilic property can be reinstated by irradiation with ultraviolet rays.

In this case, ultraviolet rays having a wavelength of 254 nm can also be used.

As described above, according to the liquid immersion member of the present embodiment, the ta-C:Ti film is formed in at least a portion of the region which comes into contact with the liquid LQ of the liquid immersion member 6. Thereby, in the region having the ta-C:Ti film formed therein, even when a chemical affinity with the resist component or the topcoat component eluted into the adjoining liquid LQ is low, and the wetting and drying of the liquid LQ are repeated, the adhesion and reprecipitation of the resist component or the topcoat component in the liquid LQ are not likely to occur. Therefore, it is possible to effectively reduce the number of exposure defects due to the reprecipitation of the resist component or the topcoat component on the surface of the liquid immersion member 6 in the region which is in contact with the liquid LQ, the peeling-off of the reprecipitates, and the attachment thereof to the surface of the substrate P during exposure.

In addition, according to the liquid immersion member of the present embodiment, since the reprecipitation of the resist component or the topcoat component on the liquid immersion member 6 is not likely to occur, it is possible to reduce the frequency of cleaning work of the liquid immersion member 6. In addition, the ta-C:Ti film is formed on the surface of the liquid immersion member 6. Thereby, even when the reprecipitation of the resist component or the topcoat component is caused by a repeated exposure process, a low chemical affinity between the surface of the liquid immersion member 6 and the resist component or the topcoat component can cause these components to be dissolved and washed by a water flow, and a weak adhesion force therebetween can also cause the cleaning work time of the reprecipitates to be shortened. Therefore, according to the present embodiment, since the frequency and time of the cleaning work can be reduced, it is possible to shorten the downtime of the liquid immersion exposure apparatus, and to reduce deteriorations in productivity.

Further, according to the method of manufacturing the liquid immersion member of the present embodiment, it is possible to effectively reduce the number of exposure defects, and to provide a liquid immersion member capable of reducing deteriorations in productivity by reducing the frequency and time of cleaning work.

Second Embodiment

Next, a second embodiment will be described. In the following description, configuration portions which are the same as or equivalent to those of the above-mentioned embodiment are denoted by the same reference numerals and signs, and thus the description thereof will be simplified or omitted.

Figure 10:
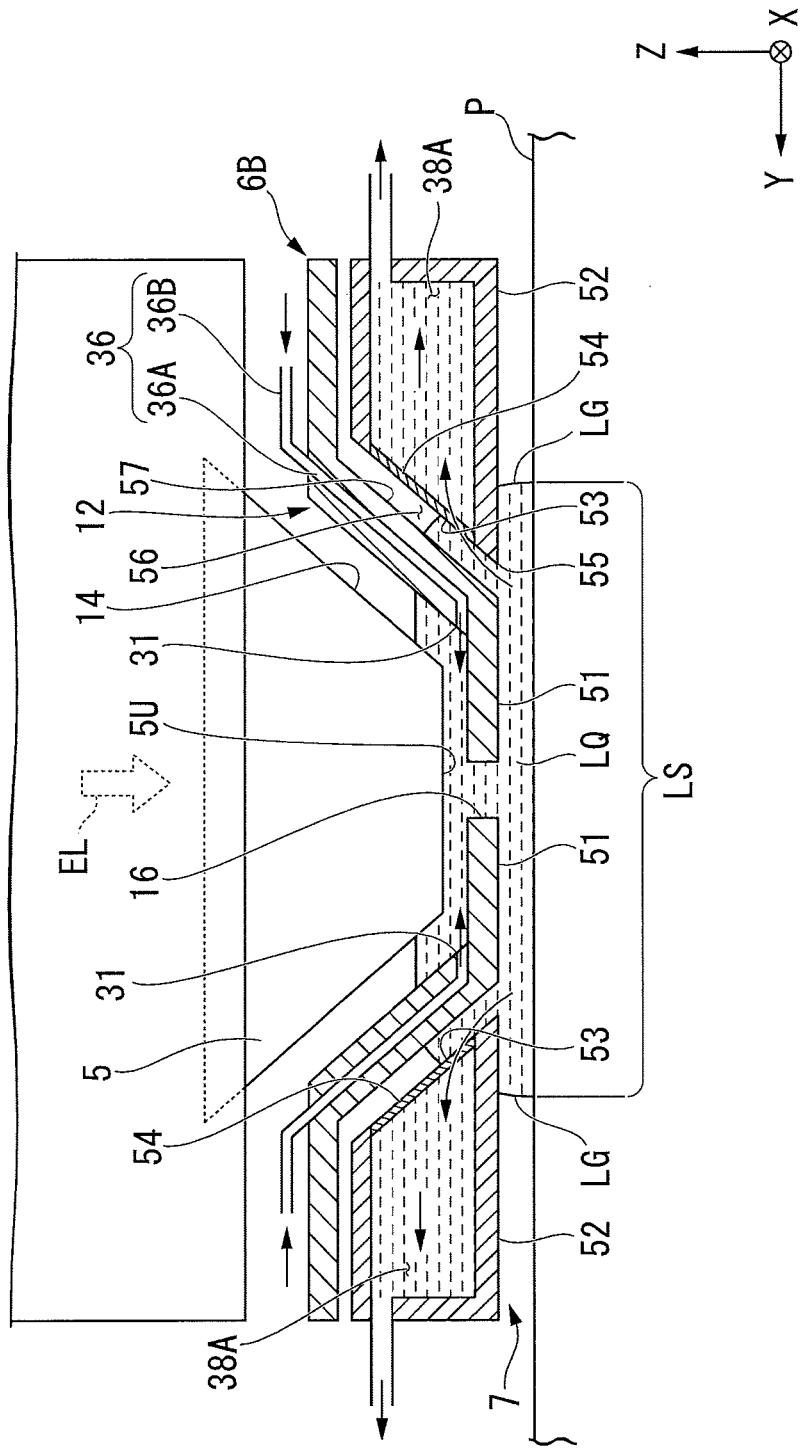
FIG. 10 is a cross-sectional side view showing the vicinity of a liquid immersion member according to a second embodiment.

FIG. 10 is a cross-sectional side view showing a portion of a liquid immersion member 6B according to the second embodiment. As shown in FIG. 10, the lower surface 7 of the liquid immersion member 6B is constituted by a first land surface 51, and a second land surface 52 provided on the outer circumference of the first land surface, and the first land surface 51 and the second land surface 52 are disposed in substantially the same plane (are flush with each other). The supply channel 36A is formed by the side plate portion 12 provided facing the outer circumferential surface 14 of the terminal optical element 5, and an outer circumferential surface 57. A recovery port 53 includes the surface of a mesh member 54, and is disposed so as to face the outer circumferential surface 57 without facing the substrate P. In the liquid immersion member 6B of the present embodiment, the liquid LQ having flowed into a void 56 through a first opening 55 formed between the first land surface 51 and the second land surface 52 is suctioned and recovered through the mesh member 54 of the recovery port 53. Meanwhile, in the present embodiment, the liquid immersion member 6B having a configuration as disclosed in Japanese Unexamined Patent Application, First Publication No. 2008-182241 may be used.

In the present embodiment, among configuration members of the liquid immersion member 6B, regions having the ta-C:Ti film formed on the surfaces thereof include configuration members of regions which come into contact with the liquid LQ, as is the case with the first embodiment. The configuration members are, for example, the recovery port 53, the mesh member 54, the first land surface 51, the second land surface 52, and the outer circumferential surface 57. Above all, it is preferable that the ta-C:Ti film be formed on the second land surface 52 which comes into contact with an interface LG of the liquid LQ, and the mesh member 54 which is the recovery port 53 that recovers the liquid LQ. Meanwhile, a configuration of the mesh member 54 and a method of forming the ta-C:Ti film on the mesh member 54 are the same as those in the first embodiment.

In the present embodiment, since the reprecipitation of the resist component or the topcoat component in the liquid LQ can also be suppressed, it is possible to reduce the number of exposure defects caused by the adhesion of the reprecipitates to the substrate P due to the peeling-off thereof. In addition, since the frequency of cleaning processes can be reduced by suppressing the reprecipitation of the resist component or the topcoat component, it is possible to reduce deteriorations in productivity.

Third Embodiment

Next, a third embodiment will be described. In the following description, configuration portions which are the same as or equivalent to those of the above-mentioned embodiment are denoted by the same reference numerals and signs, and thus the description thereof will be simplified or omitted.

Figure 11:
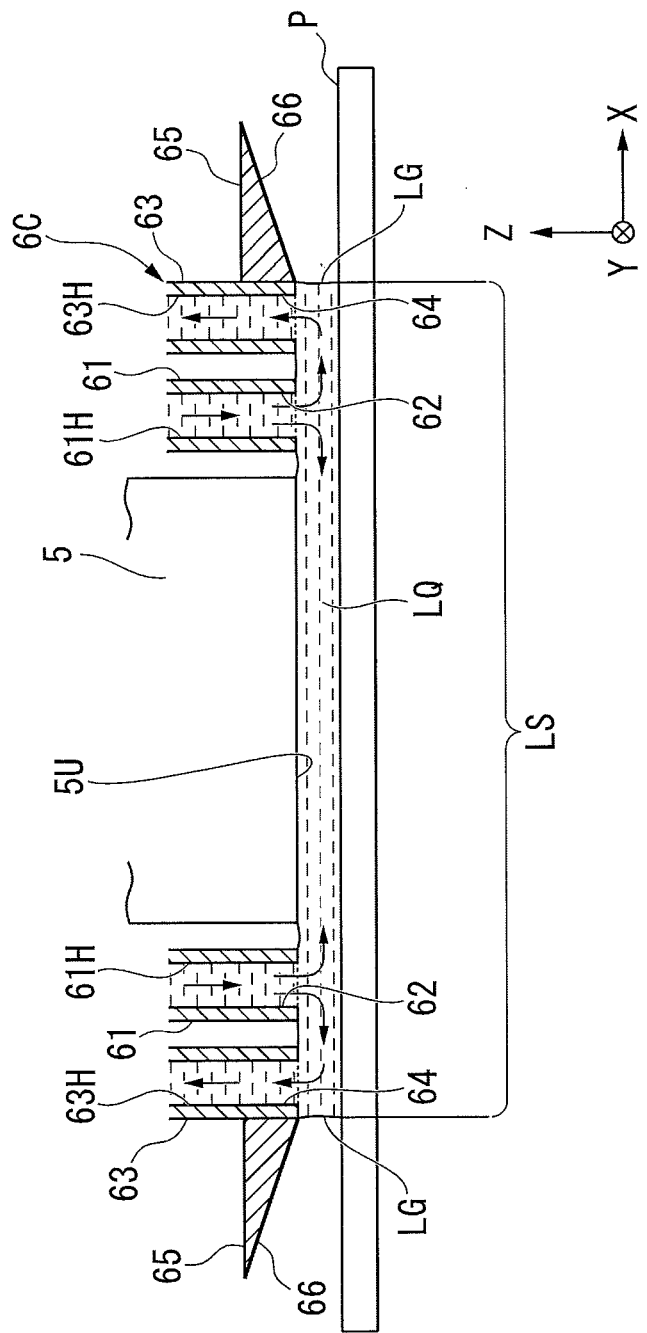
FIG. 11 is a cross-sectional side view showing the vicinity of a liquid immersion member according to a third embodiment.

FIG. 11 is a cross-sectional side view showing a portion of a liquid immersion member 6C according to the third embodiment. As shown in FIG. 11, in the liquid immersion member 6C, a supply channel 61H formed by a supply member 61 installed around the terminal optical element 5 is configured such that a supply port 62 faces the substrate P. A recovery channel 63H formed on the outer circumference of the supply member 61 by a recovery member 63 is configured such that a recovery port 64 faces the substrate P. A trap member 65 is installed on the outer circumference of the recovery member 63. A trap surface 66 is a surface (that is a lower surface) of the trap member 65 which is directed toward the substrate P side, and is inclined with respect to the horizontal plane as shown in FIG. 6. In the liquid immersion member 6C of the present embodiment, the liquid LQ supplied from the supply port 62 to the substrate P in a substantially vertical direction to the substrate surface is supplied so as to be wet and spread between the lower surface 5U of the terminal optical element 5 and the substrate P. In addition, the liquid LQ of the liquid immersion space LS is suctioned and recovered by the recovery port 64 in a substantially vertical direction from the substrate surface. Meanwhile, in the present embodiment, the liquid immersion member 6C having a configuration as disclosed in Japanese Unexamined Patent Application, First Publication No. 2005-109426 may be used.

In the present embodiment, among configuration members of the liquid immersion member 6C, regions having the ta-C:Ti film formed on the surfaces thereof include configuration members of regions which come into contact with the liquid LQ, as is the case with the first embodiment. The configuration members may be any of the supply member 61, the recovery member 63, and the trap member 65 (trap surface 66).

In the present embodiment, since the reprecipitation of the resist component or the topcoat component in the liquid LQ can also be suppressed, it is possible to reduce the number of exposure defects caused by the adhesion of the reprecipitates to the substrate P due to the peeling-off thereof. In addition, since the frequency of cleaning processes can be reduced by suppressing the reprecipitation of the resist component or the topcoat component, it is possible to reduce deteriorations in productivity.

Fourth Embodiment

Next, a fourth embodiment will be described. In the following description, configuration portions which are the same as or equivalent to those of the above-mentioned embodiment are denoted by the same reference numerals and signs, and thus the description thereof will be simplified or omitted.

Figure 12:
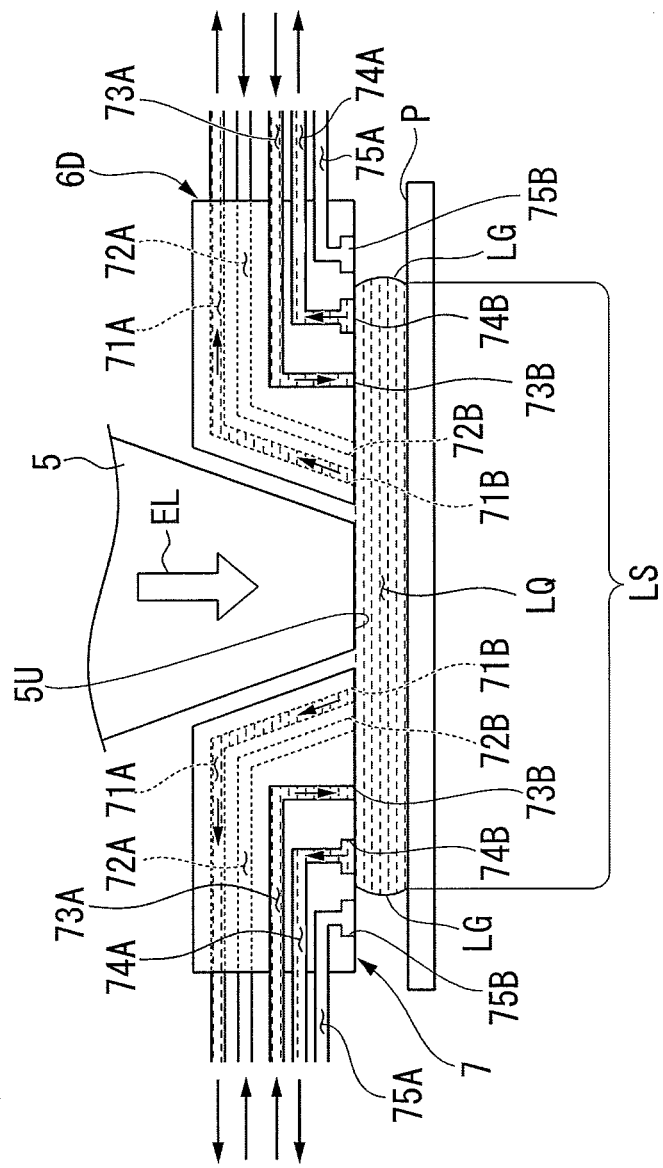
FIG. 12 is a cross-sectional side view showing the vicinity of a liquid immersion member according to a fourth embodiment.

FIG. 12 is a cross-sectional side view showing a portion of a liquid immersion member 6D according to a fourth embodiment. As shown in FIG. 12, in the liquid immersion member 6D, a pressure regulating recovery channel 71A, a pressure regulating supply channel 72A, a supply channel 73A, a recovery channel 74A, and an auxiliary recovery channel 75A are formed in this order from the inner circumferential side of the liquid immersion member 6D toward the outer circumferential side in the vicinity of the terminal optical element 5. On the lower surface 7 of the liquid immersion member 6D, a pressure regulating recovery port 71B, a pressure regulating supply port 72B, a supply port 73B, a recovery port 74B, and an auxiliary recovery port 75B are formed in this order from the inner circumferential side of the liquid immersion member 6D toward the outer circumferential side in the vicinity of the terminal optical element 5 so as to face the substrate P.

In the liquid immersion member 6D of the present embodiment, the liquid LQ supplied from the supply port 73B is wet and spread on the substrate P, to form a liquid immersion region LS. The liquid LQ of the liquid immersion region LS is suctioned and recovered from the recovery port 74B. When the liquid LQ of the liquid immersion region LS on the substrate P fails to be recovered in the recovery port 74B, the liquid which has not been recovered flows outside the recovery port 74B, but can be recovered through the auxiliary recovery port 75B. In addition, during the exposure of the substrate P, the liquid LQ of the liquid immersion space LS is recovered from the pressure regulating recovery port 71B, or the liquid LQ is supplied from the pressure regulating supply port 72B to the liquid immersion space LS, thereby allowing the liquid immersion region LS to be controlled to a desired shape and pressure. Meanwhile, in the present embodiment, the liquid immersion member 6D having a configuration as disclosed in Japanese Unexamined Patent Application, First Publication No. 2005-223315 may be used.

In the present embodiment, among configuration members of the liquid immersion member 6D, regions having the ta-C:Ti film formed on the surfaces thereof include configuration members disposed in regions which come into contact with the liquid LQ, as is the case with the first embodiment.

In the present embodiment, since the reprecipitation of the resist component or the topcoat component in the liquid LQ can also be suppressed, it is possible to reduce the number of exposure defects caused by the adhesion of the reprecipitates to the substrate P due to the peeling-off thereof. In addition, since the frequency of cleaning processes can be reduced by suppressing the reprecipitation of the resist component or the topcoat component, it is possible to reduce deteriorations in productivity.

Fifth Embodiment

Next, a fifth embodiment will be described. In the following description, configuration portions which are the same as or equivalent to those of the above-mentioned embodiment are denoted by the same reference numerals and signs, and thus the description thereof will be simplified or omitted.

Figure 13:
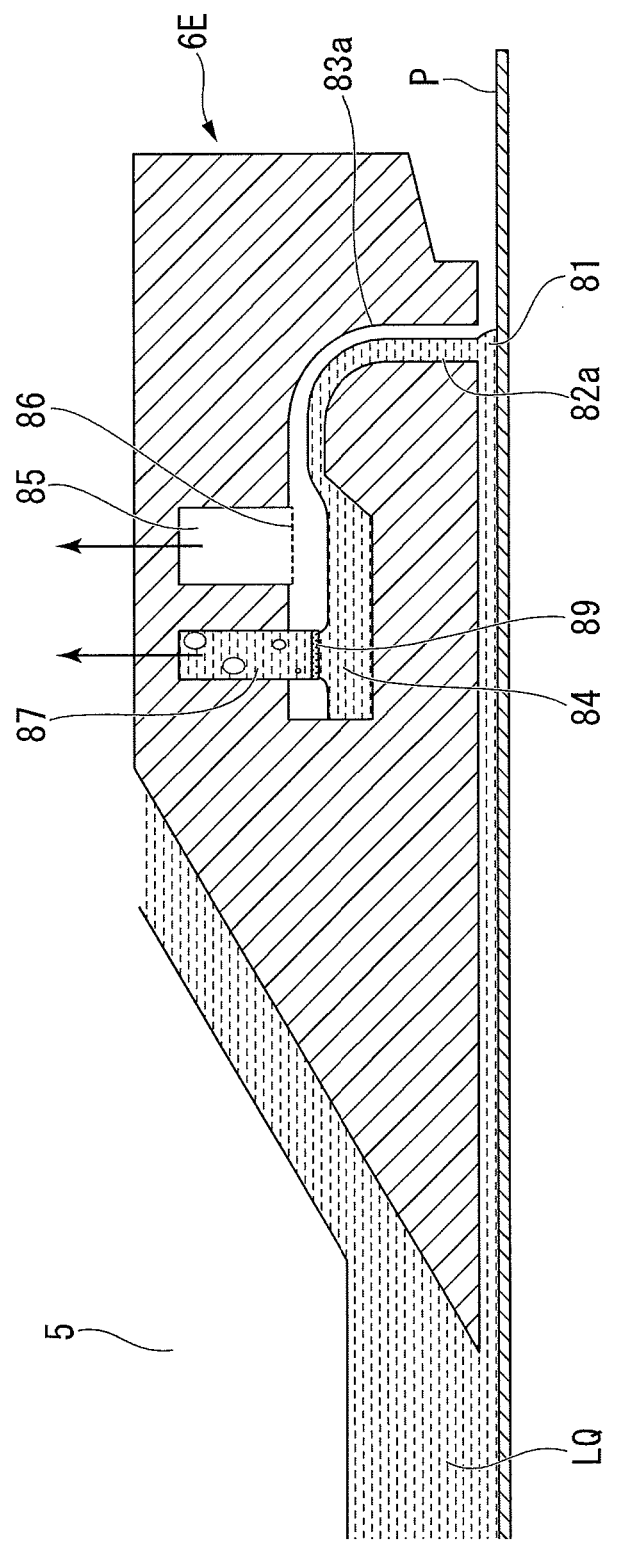
FIG. 13 is a cross-sectional side view showing the vicinity of a liquid immersion member according to a fifth embodiment.

FIG. 13 is a cross-sectional side view showing a portion of a liquid immersion member 6E according to the fifth embodiment. As shown in FIG. 13, in the liquid immersion member 6E, a gap 81 is defined between a wall 82a and a wall 83a, and a separation chamber 84 provided continuously with the gap 81 is included. The liquid LQ is introduced into the separation chamber 84 through the gap 81. Liquid and gas are separated by the separation chamber 84.

A gas recovery path 85 and a liquid recovery path 87 are provided continuously with the separation chamber 84. The gas separated by the separation chamber 84 is recovered from the gas recovery path 85 through a film 86. The separated liquid is recovered from the liquid recovery path 87.

In the present embodiment, among configuration members of the liquid immersion member 6E, regions having the ta-C:Ti film found on the surfaces thereof include configuration members disposed in regions which come into contact with the liquid LQ, as is the case with the first embodiment.

Particularly, in the present embodiment, it is preferable that a mesh member 89 having the ta-C:Ti film formed therein be disposed in an inlet portion of the liquid recovery path 87.

In the present embodiment, since the reprecipitation of the resist component or the topcoat component in the liquid LQ can also be suppressed, it is possible to reduce the number of exposure defects caused by the adhesion of the reprecipitates to the substrate P due to the peeling-off thereof. In addition, since the frequency of cleaning processes can be reduced by suppressing the reprecipitation of the resist component or the topcoat component, it is possible to reduce deteriorations in productivity.

Sixth Embodiment

Next, a sixth embodiment will be described. In the following description, configuration portions which are the same as or equivalent to those of the above-mentioned embodiment are denoted by the same reference numerals and signs, and thus the description thereof will be simplified or omitted.

Figure 14:
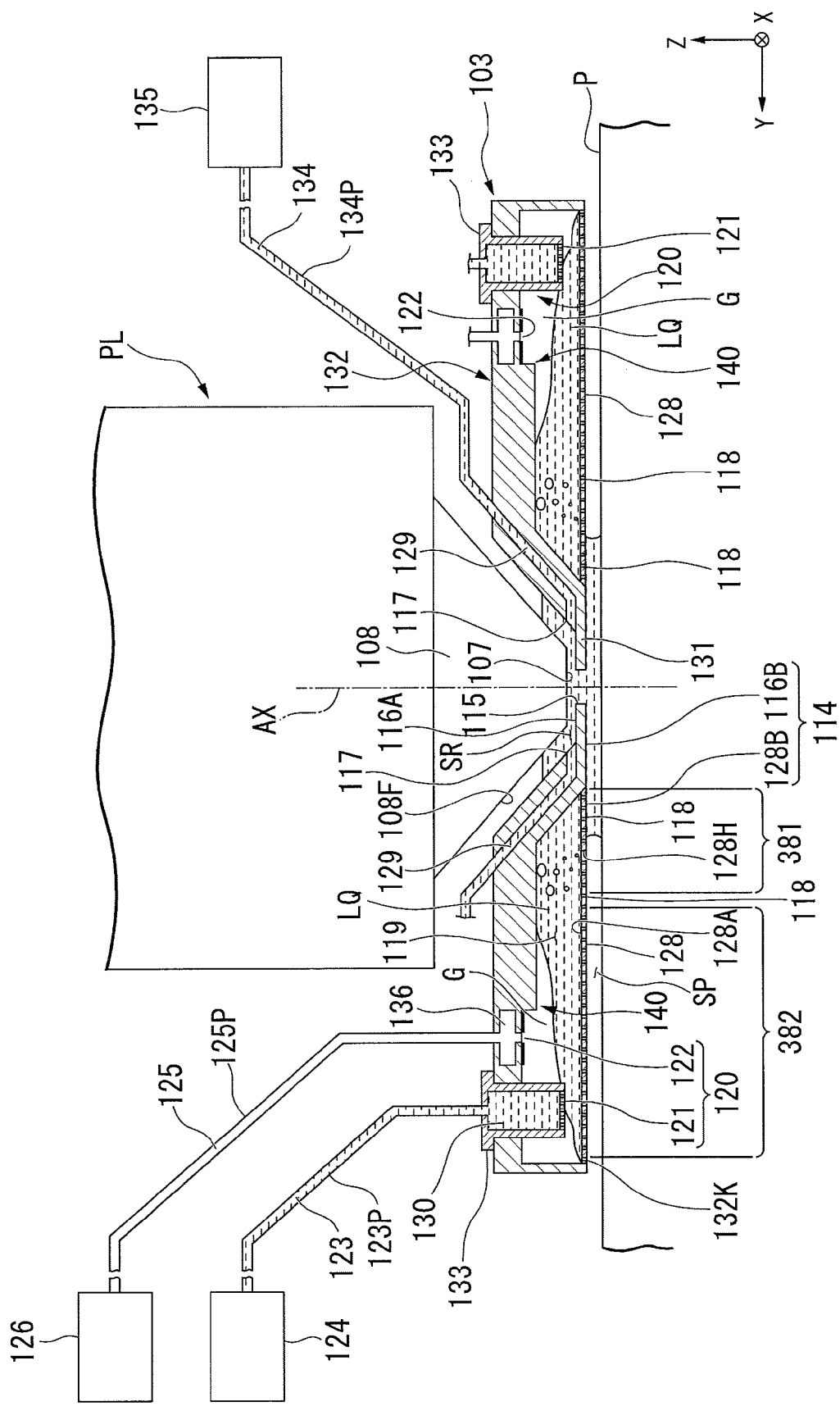
FIG. 14 is a cross-sectional side view showing the vicinity of a liquid immersion member according to a sixth embodiment.
Figure 15:
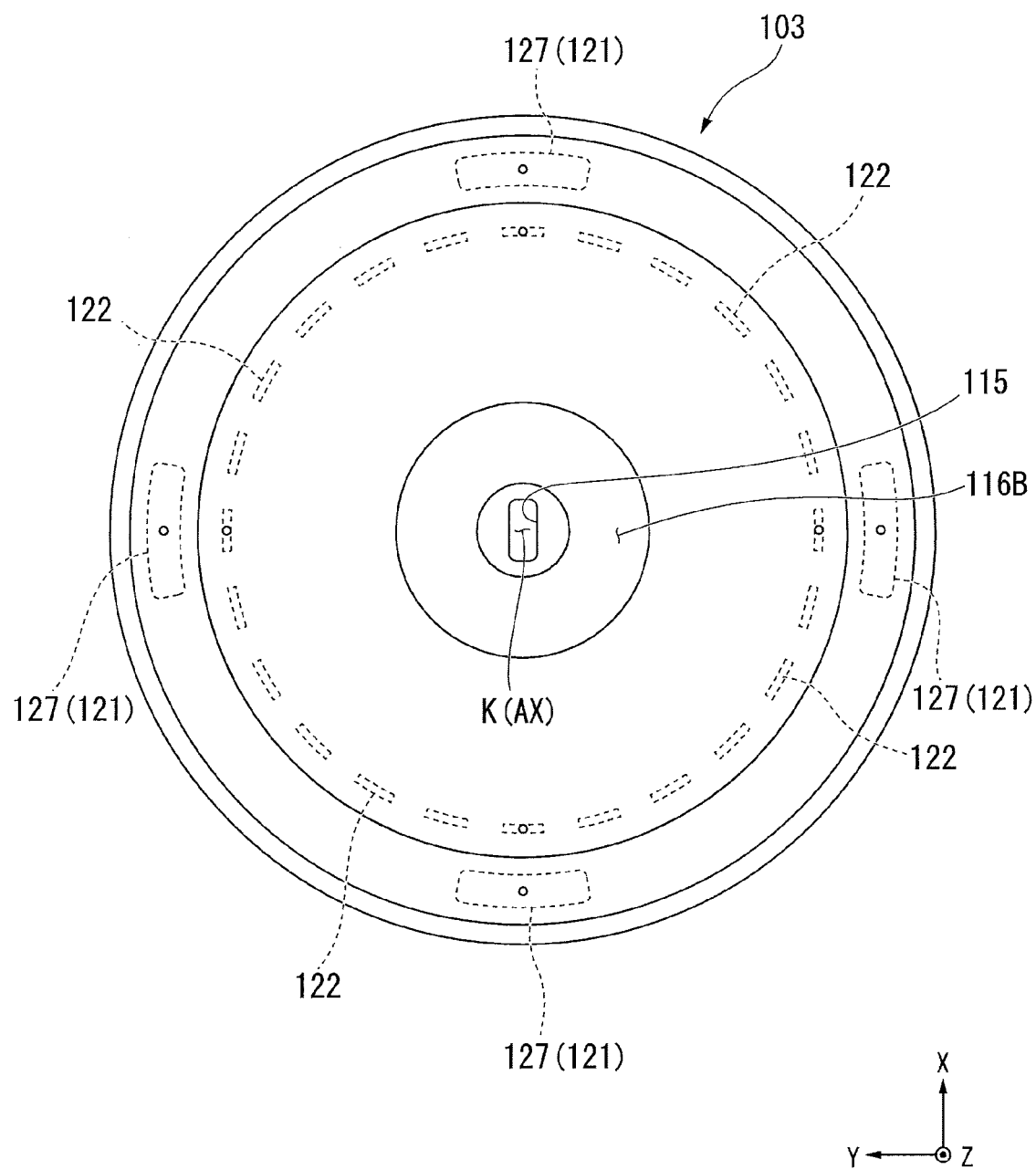
FIG. 15 is a diagram when the liquid immersion member shown in FIG. 14 is seen from the upper side.
Figure 16:
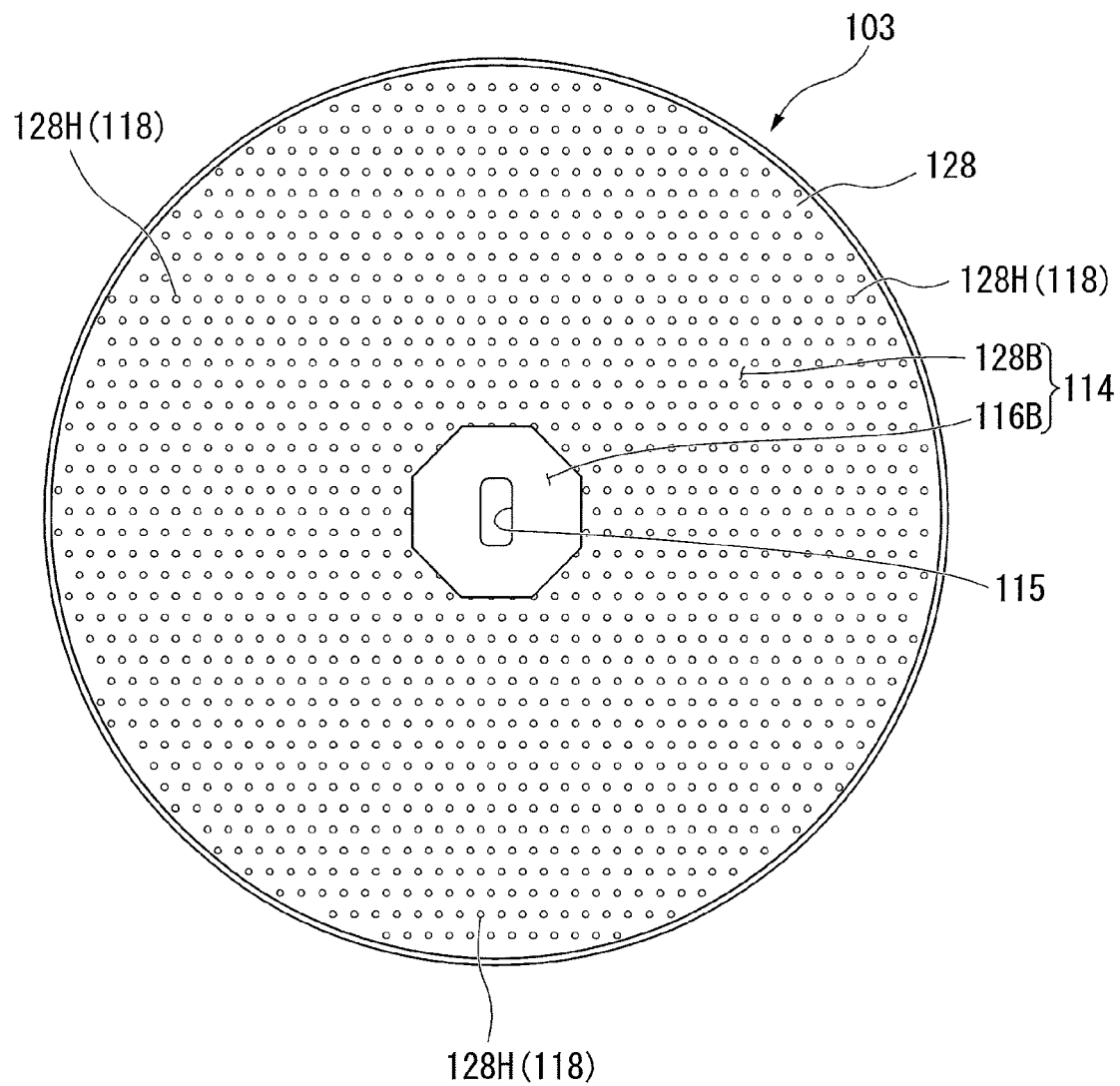
FIG. 16 is a diagram when the liquid immersion member shown in FIG. 14 is seen from the lower side.
Figure 17:
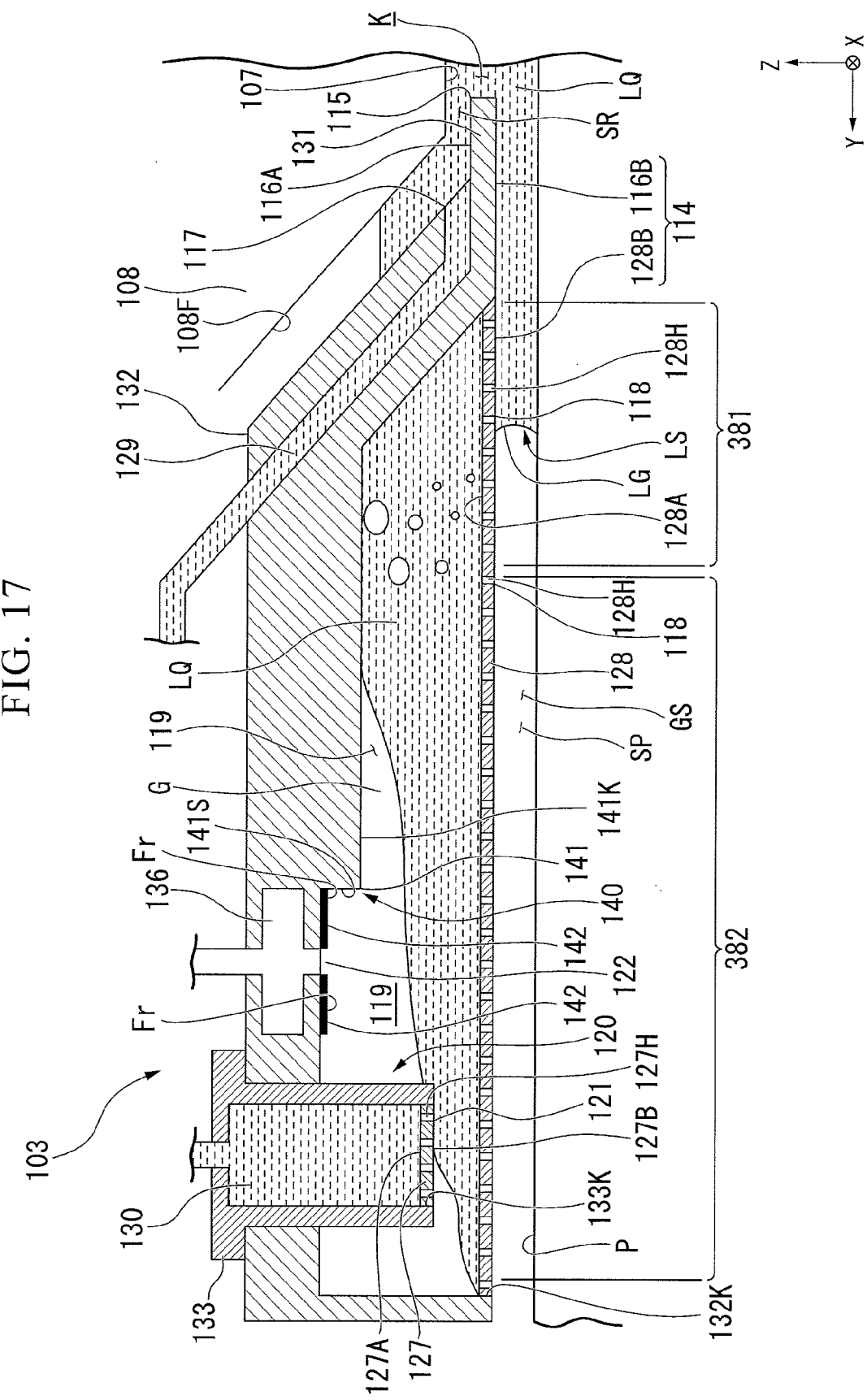
FIG. 17 is an enlarged view showing a portion of the liquid immersion member shown in FIG. 14.

FIG. 14 is a cross-sectional side view showing an example of a liquid immersion member 103 according to the sixth embodiment, FIG. 15 is a diagram when the liquid immersion member 103 is seen from the upper side (+Z side), FIG. 16 is a diagram when the liquid immersion member 103 is seen from the lower side (−Z side), and FIG. 17 is an enlarged view showing a portion of FIG. 14.

In the present embodiment, the liquid immersion member 103 includes a plate portion 131 of which at least a portion is disposed so as to face an emission surface 107, a main body portion 132 of which at least a portion is disposed so as to face a lateral side 108F of a terminal optical element 108, and a channel forming member 133. In the present embodiment, the plate portion 131 and the main body portion 132 are formed integrally with each other. In the present embodiment, the channel forming member 133 is different from the plate portion 131 and the main body portion 132. In the present embodiment, the channel forming member 133 is supported by the main body portion 132. Meanwhile, the channel forming member 133, the plate portion 131 and the main body portion 132 may be formed integrally with each other.

Meanwhile, the lateral side 108F is disposed in the vicinity of the emission surface 107. In the present embodiment, the lateral side 108F is inclined upward toward the outside with respect to a radial direction for the optical path K. Meanwhile, the radial direction for the optical path K includes a radial direction for the optical axis AX of the projection optical system PL, and includes a direction perpendicular to the Z-axis.

The liquid immersion member 103 has an opening 115 at a position facing the emission surface 107. The exposure light EL emitted from the emission surface 107 passes through the opening 115, and the substrate P can be irradiated with the exposure light. In the present embodiment, the plate portion 131 includes an upper surface 116A facing at least a portion of the emission surface 107, and a lower surface 116B capable of facing the surface of the substrate P. The opening 115 includes a hole which is formed so as to link the upper surface 116A to the lower surface 116B. The upper surface 116A is disposed in the vicinity of the upper end of the opening 115, and the lower surface 116B is disposed in the vicinity of the lower end of the opening 115.

In the present embodiment, the upper surface 116A is flat. The upper surface 116A is substantially parallel to the XY plane. Meanwhile, at least a portion of the upper surface 116A may be inclined with respect to the XY plane, and may include a curved surface. In the present embodiment, the lower surface 116B is flat. The lower surface 116B is substantially parallel to the XY plane. Meanwhile, at least a portion of the lower surface 116B may be inclined with respect to the XY plane, and may include a curved surface. The lower surface 116B holds the liquid LQ between the surface of the substrate P and the lower surface.

As shown in FIG. 16, in the present embodiment, the outer shape of the lower surface 116B is octagonal. Meanwhile, the outer shape of the lower surface 116B may be an arbitrary polygonal shape such as, for example, a quadrilateral shape or a hexagonal shape. In addition, the outer shape of the lower surface 116B may be circular, elliptical or the like.

The liquid immersion member 103 includes a supply port 117 capable of supplying the liquid LQ, a recovery port 118 capable of recovering the liquid LQ, a recovery channel 119 in which the liquid LQ recovered from the recovery port 118 flows, and a discharge portion 120 that separates and discharges the liquid LQ and gas G of the recovery channel 119.

The supply port 117 can supply the liquid LQ to the optical path K. In the present embodiment, the supply port 117 supplies the liquid LQ to the optical path K in at least a portion of the exposure of the substrate P. The supply port 117 is disposed in the vicinity of the optical path K so as to face the optical path K. In the present embodiment, the supply port 117 supplies the liquid LQ to a space SR between the emission surface 107 and the upper surface 116A. At least a portion of the liquid LQ supplied from the supply port 117 to the space SR is supplied to the optical path K, and is supplied onto the substrate P through the opening 115. Meanwhile, at least a portion of at least one supply port 117 may face the lateral side 108F.

The liquid immersion member 103 includes a supply channel 129 connected to the supply port 117. At least a portion of the supply channel 129 is formed inside the liquid immersion member 103. In the present embodiment, the supply port 117 includes an opening formed at one end of the supply channel 129. The other end of the supply channel 129 is connected to a liquid supply device 135 through a channel 134 which is formed by a supply tube 134P.

The liquid supply device 135 can send out the liquid LQ which is cleaned and temperature-regulated. The liquid LQ sent out from the liquid supply device 135 is supplied to the supply port 117 through the channel 134 and the supply channel 129. The supply port 117 supplies the liquid LQ from the supply channel 129 to the optical path K (space SR).

The recovery port 118 can recover at least a portion of the liquid LQ on the substrate P (on the object). The recovery port 118 recovers at least a portion of the liquid LQ on the substrate P in the exposure of the substrate P. The recovery port 118 is directed toward the −Z direction. In at least a portion of the exposure of the substrate P, the surface of the substrate P faces the recovery port 118.

In the present embodiment, the liquid immersion member 103 includes a first member 128 having the recovery port 118. The first member 128 includes a first surface 128B, a second surface 128A directed toward a direction different from that of the first surface 128B, and a plurality of holes 128H that link the first surface 128B to the second surface 128A. In the present embodiment, the recovery port 118 includes the holes 128H of the first member 128. In the present embodiment, the first member 128 is a mesh member (porous member) having a plurality of holes (openings or pores) 12811. Meanwhile, the first member 128 may be a mesh filter in which numerous small holes are formed in a mesh shape. That is, various members having holes capable of recovering the liquid LQ can be applied to the first member 128.

At least a portion of the recovery channel 119 is formed inside the liquid immersion member 103. In the present embodiment, an opening 132K is formed at the lower end of the recovery channel 119. The opening 132K is disposed in at least a portion of the vicinity of the lower surface 116B. The opening 132K is formed at the lower end of the main body portion 132. The opening 132K is directed downward (−Z direction). In the present embodiment, the first member 128 is disposed in the opening 132K. The recovery channel 119 includes a space between the main body portion 132 and the first member 128.

The first member 128 is disposed in at least a portion of the vicinity of the optical path K (lower surface 116B). In the present embodiment, the first member 128 is disposed in the vicinity of the optical path K. Meanwhile, the annular first member 128 may be disposed in the vicinity of the optical path K (lower surface 116B), and a plurality of first members 128 may be discretely disposed in the vicinity of the optical path K (lower surface 116B).

In the present embodiment, the first member 128 is a plate-shaped member. The first surface 128B is one surface of the first member 128, and the second surface 128A is the other surface of the first member 128. In the present embodiment, the first surface 128B faces a space SP on the lower side (−Z direction side) of the liquid immersion member 103. The space SP includes, for example, a space between a lower surface 114 of the liquid immersion member 103 and a surface of an object (such as the substrate P) facing the lower surface 114 of the liquid immersion member 103. When the liquid immersion space LS is formed on the object (such as the substrate P) facing the lower surface 114 of the liquid immersion member 103, the space SP includes the liquid immersion space (liquid space) LS and a gas space GS.

In the present embodiment, the first member 128 is disposed in the opening 132K so that the first surface 128B faces the space SP and the second surface 128A faces the recovery channel 119. In the present embodiment, the first surface 128B and the second surface 128A are substantially parallel to each other. The first member 128 is disposed in the opening 132K so that the second surface 128A is directed toward the +Z direction and the first surface 128B is directed toward the opposite direction (−Z direction) to the second surface 128A. In addition, in the present embodiment, the first member 128 is disposed in the opening 132K so that the first surface 128B and the second surface 128A, and the XY plane are substantially parallel to each other.

In the following description, the first surface 128B may be referred to as the lower surface 128B, and the second surface 128A may be referred to as the upper surface 128A.

Meanwhile, the first member 128 may not be plate-shaped. In addition, the lower surface 128B and the upper surface 128A may be non-parallel to each other. In addition, at least a portion of the lower surface 128B may be inclined with respect to the XY plane, and may include a curved surface. In addition, at least a portion of the upper surface 128A may be inclined with respect to the XY plane, and may include a curved surface.

The hole 128H is formed so as to link the lower surface 128B to the upper surface 128A. A fluid (including at least one of the gas G and the liquid LQ) can flow through the hole 128H of the first member 128. In the present embodiment, the recovery port 118 includes an opening of the lower end of the hole 128H on the lower surface 128B side. The lower surface 128B is disposed in the vicinity of the lower end of the hole 128H, and the upper surface 128A is disposed in the vicinity of the upper end of the hole 128H.

The recovery channel 119 is connected to the hole 128H (recovery port 118) of the first member 128. The first member 128 recovers at least a portion of the liquid LQ on the substrate P (object) facing the lower surface 128B, from the hole 128H (recovery port 118). The liquid LQ recovered from the hole 128H of the first member 128 flows through the recovery channel 119.

In the present embodiment, the lower surface 114 of the liquid immersion member 103 includes the lower surface 116B and the lower surface 128B. In the present embodiment, the lower surface 128B is disposed in at least a portion of the vicinity of the lower surface 116B. In the present embodiment, the annular lower surface 128B is disposed in the vicinity of the lower surface 116B. Meanwhile, a plurality of lower surfaces 128B may be discretely disposed in the vicinity of the lower surface 116B (optical path K).

In the present embodiment, the first member 128 includes a first portion 381 and a second portion 382. In the present embodiment, the second portion 382 is disposed outside the first portion 381 with respect to a radial direction for the optical path K. In the present embodiment, the second portion 382 is configured such that the inflow of the gas G from the space SP through the hole 128H to the recovery channel 119 is suppressed further than in the first portion 381. In the present embodiment, the width of the first portion 381 is smaller than the width of the second portion 382 with respect to a radial direction for the optical path K.

In the present embodiment, in the second portion 382, the inflow resistance of the gas G from the space SP through the hole 128H to the recovery channel 119 is greater than in the first portion 381.

The first portion 381 and the second portion 382 have a plurality of holes 128H, respectively. For example, in a state where the liquid immersion space LS is formed in the space SP, there is a possibility that some of the holes 128H out of the plurality of holes 128H of the first portion 381 may come into contact with the liquid LQ of the liquid immersion space LS, and that some of the holes 128H may not come into contact with the liquid LQ of the liquid immersion space LS. In addition, there is a possibility that some of the holes 128H out of the plurality of holes 128H of the second portion 382 may come into contact with the liquid LQ of the liquid immersion space LS, and that some of the holes 128H may not come into contact with the liquid LQ of the liquid immersion space LS.

In the present embodiment, the first portion 381 can recover the liquid LQ from the hole 128H that comes into contact with the liquid LQ (liquid LQ on the substrate P) of the space SP to the recovery channel 119. In addition, the first portion 381 suctions the gas G from the hole 128H which does not come into contact with the liquid LQ to the recovery channel 119.

That is, the first portion 381 can recover the liquid LQ of the liquid immersion space LS from the hole 128H facing the liquid immersion space LS to the recovery channel 119, and suctions the gas G from the hole 128H facing the gas space GS located outside the liquid immersion space LS to the recovery channel 119.

In other words, the first portion 381 can recover the liquid LQ of the liquid immersion space LS from the hole 128H facing the liquid immersion space LS to the recovery channel 119, and suctions the gas G from the hole 128H which does not face the liquid immersion space LS to the recovery channel 119.

That is, when the interface LG of the liquid LQ of the liquid immersion space LS is present between the first portion 381 and the substrate P, the first portion 381 recovers the liquid LQ to the recovery channel 119 together with the gas G. Meanwhile, in the interface LG, both the liquid LQ and the gas G may be suctioned from the hole 128H facing the liquid immersion space LS and the gas space GS.

The second portion 382 can recover the liquid LQ from the hole 128H which comes into contact with the liquid LQ (liquid LQ on the substrate P) of the space SP to the recovery channel 119. In addition, the second portion 382 is configured such that the inflow of the gas G from the hole 128H which does not come into contact with the liquid LQ to the recovery channel 119 is suppressed.

That is, the second portion 382 can recover the liquid LQ of the liquid immersion space LS from the hole 128H facing the liquid immersion space LS to the recovery channel 119, and is configured such that the inflow of the gas G from the hole 128H facing the gas space GS located outside the liquid immersion space LS to the recovery channel 119 is suppressed.

In the present embodiment, the second portion 382 recovers substantially only the liquid LQ to the recover channel 119, and does not recover the gas G to the recovery channel 119.

In the present embodiment, among configuration members of the liquid immersion member, regions having the ta-C:Ti film formed on the surfaces thereof include configuration members disposed in regions which come into contact with the liquid LQ, as is the case with the first embodiment.

In the present embodiment, since the reprecipitation of the resist component or the topcoat component in the liquid LQ can also be suppressed, it is possible to reduce the number of exposure defects caused by the adhesion of the reprecipitates to the substrate P due to the peeling-off thereof. In addition, since the frequency of cleaning processes can be reduced by suppressing the reprecipitation of the resist component or the topcoat component, it is possible to reduce deteriorations in productivity.

Particularly, in the liquid immersion member of the present embodiment, the recovery pressure of liquid is high. The ta-C:Ti film according to the embodiment of the present invention is used in such a liquid immersion member, thereby allowing the above-mentioned effect to be exhibited more sufficiently.

Meanwhile, in the each embodiment mentioned above, the optical path on the emission side (image plane side) of the terminal optical element 5 of the projection optical system PL is filled with the liquid LQ. However, as disclosed in, for example, PCT International Publication No. WO2004/019128, it is possible to adopt the projection optical system PL in which the optical path on the incident side (object plane side) of the terminal optical element is also filled with the liquid LQ.

Meanwhile, in the each embodiment mentioned above, water is used as the liquid LQ, but liquids other than water may be used.

In addition, in the present embodiment, the ta-C:Ti film is provided on the surface of the liquid immersion member 6, and is set to have a hydrophilic property by irradiation with ultraviolet rays, but a portion of the liquid immersion member may be set to have a water-repellent property. The ta-C:Ti film having a hydrophilic property is provided in a portion which comes into contact with the liquid, and the ta-C:Ti film having a water-repellent property is provided on the outer circumference thereof, thereby allowing an effect of holding the liquid in the portion having a hydrophilic property to be expected. Meanwhile, it is possible to combine the portion having a water-repellent property with the portion having a hydrophilic property by irradiation with ultraviolet rays, in a state where the ta-C:Ti film is formed and then is covered with a light-shielding member.

Meanwhile, as the substrate P of each of the present embodiments mentioned above, not only a semiconductor wafer for a semiconductor device, but also a glass substrate for a display device, a ceramic wafer for a thin-film magnetic head, or an original plate (synthetic silica, silicon wafer) of a mask or a reticle used in the exposure apparatus and the like are applied.

The exposure apparatus EX can also be applied to a step-and-repeat type projection exposure apparatus (stepper) in which the sequential step movement is performed on the substrate P by collectively exposing the patterns of the mask M in the state where the mask M and the substrate P are stopped, in addition to a step-and-scan type scanning exposure apparatus (scanning stepper) that scans and exposes the pattern of the mask M by synchronously moving the mask M and the substrate P.

Further, in the step-and-repeat type exposure, after a reduced image of a first pattern is transferred onto the substrate P using the projection optical system in the state where the first pattern and the substrate P are substantially stopped, a reduced image of a second pattern may be partially overlapped with the first pattern using the projection optical system to perform collective exposure onto the substrate P in the state where the second pattern and the substrate P are substantially stopped (stitch-type collective exposure apparatus). In addition, the stitch-type exposure apparatus can also be applied to a step-and-stitch type exposure apparatus which partially overlaps at least two patterns with each other on the substrate P to transfer them, and sequentially moves the substrate P.

In addition, for example, as disclosed in U.S. Pat. No. 6,611,316, the present invention can also be applied to an exposure apparatus which synthesizes patterns of two masks on the substrate through the projection optical system, and substantially simultaneously double-exposes one shot region on the substrate by one-time scanning exposure and the like. In addition, the present invention can also be applied to a proximity-type exposure apparatus, a mirror projection aligner and the like.

In addition, the exposure apparatus EX may be a twin stage type exposure apparatus which includes a plurality of substrate stages, as disclosed in, for example, U.S. Pat. No. 6,341,007, U.S. Pat. No. 6,208,407, U.S. Pat. No. 6,262,796 and the like. In this case, a recovery channel which has a recovery port disposed at the end thereof and which is provided with a trapping surface may be provided in each of the plurality of substrate stages, and may be provided in some of the substrate stages.

In addition, the exposure apparatus EX may be an exposure apparatus which includes a substrate stage that holds a substrate and a measurement stage in which a reference member having a reference mark formed therein and/or various photoelectronic sensors are mounted and which does not hold the substrate to be exposed, as disclosed in, for example, U.S. Pat. No. 6,897,963, United States Patent Application, Publication No. 2007/0,127,006 and the like. In addition, the above exposure apparatus can also be applied to an exposure apparatus including a plurality of substrate stages and measurement stages. In this case, a recovery channel which has a recovery port disposed at the end thereof and which is provided with a trapping surface may be disposed in the measurement stage.

The type of exposure apparatus EX is also not limited to a semiconductor device fabrication exposure apparatus that exposes the pattern of a semiconductor device on the substrate P, but can be widely applied to, for example, exposure apparatuses that are used to fabricate liquid crystal display devices or displays, and exposure apparatuses that are used to manufacture thin film magnetic heads, image capturing devices (CCDs), micromachines, MEMS, DNA chips, reticles or masks, and the like.

Meanwhile, in each of the present embodiments mentioned above, the position information of each of the stages is measured using an interferometer system that includes laser interferometers, but the present invention is not limited thereto; for example, an encoder system that detects a scale (diffraction grating) provided to each of the stages may be used.

Meanwhile, in the embodiments described above, an optically transmissive mask wherein a predetermined light-shielding pattern (or phase pattern or dimming pattern) is formed on an optically transmissive substrate is used; however, instead of such a mask, a variable shaped mask (also called an electronic mask, an active mask, or an image generator), wherein a transmissive pattern, a reflective pattern, or a light emitting pattern is formed based on electronic data of the pattern to be exposed, as disclosed in, for example, U.S. Pat. No. 6,778,257, may be used. In addition, instead of a variable shaped mask that includes a non-emissive type image display device, a pattern forming apparatus that includes a self-luminous type image display device may be provided.

In each of the embodiments mentioned above, although the exposure apparatus that includes the projection optical system PL has been described by way of example, the present invention can nevertheless be applied to an exposure apparatus and an exposing method that do not use the projection optical system PL. For example, the immersion space can be formed between an optical member such as a lens and the substrate, and the substrate can be irradiated with the exposure light through the optical member.

In addition, the present invention can also be applied to an exposure apparatus (lithographic system) that, by forming interference fringes on the substrate P, exposes the substrate P with a line-and-space pattern, as disclosed in, for example, PCT International Publication No. WO2001/035,168.

The exposure apparatus EX of the above-mentioned embodiments is manufactured by assembling various subsystems including each component falling within the scope of the claims so that predetermined mechanical, electrical, and optical accuracies are maintained. In order to secure these various accuracies, before and after this assembly, adjustment to achieve optical accuracy with respect to various optical systems and adjustment to achieve mechanical accuracy with respect to various mechanical systems are performed. Processes of assembling the exposure apparatus from various subsystems include the connection of mechanical components, the wiring and connection of electrical circuits, the piping and connection of pneumatic circuits, and the like, among various subsystems. There is a process of assembling each individual subsystem prior to the process of assembling the exposure apparatus from various subsystems. When the process of assembling the exposure apparatus from the various subsystems is terminated, a comprehensive adjustment is performed to ensure the various accuracies of the exposure apparatus as a whole. Meanwhile, it is preferable to manufacture the exposure apparatus in a clean room in which, for example, the temperature and the cleanliness level are controlled.

Figure 18:
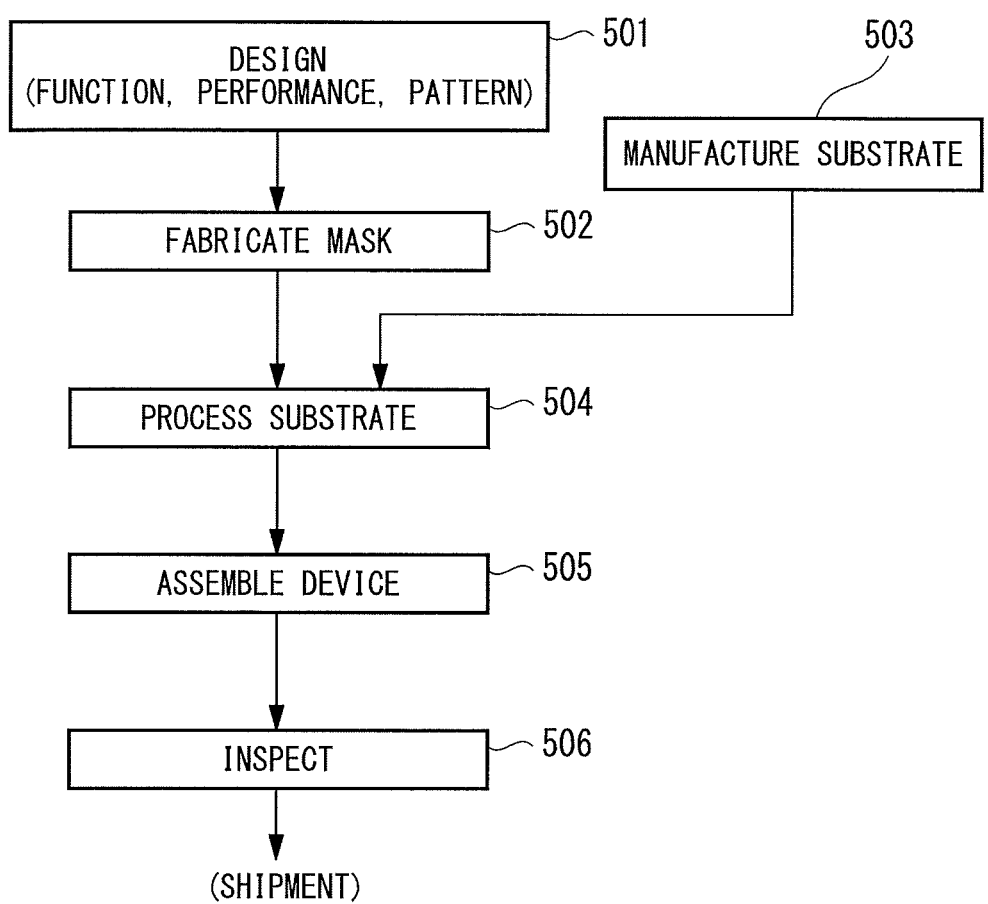
FIG. 18 is a flow diagram showing an example of a micro device manufacturing process.

As shown in FIG. 18, a micro-device such as a semiconductor device is manufactured by a step 501 of designing functions and performance of the micro-device, a step 502 of fabricating a mask (reticle) on the basis of the design step, a step 503 of manufacturing a substrate which is a base material of the device, a substrate processing step 504 including a step of exposing the substrate with exposure light from a pattern of the mask using the exposure apparatus of the above-mentioned embodiment and a step of developing the exposed substrate, a device assembling step (including manufacturing processes such as dicing, bonding, and packaging) 505, an inspecting step 506, and the like.

Meanwhile, the features of each of the embodiments mentioned above can be combined as appropriate. In addition, there may be cases in which some of the components are not used. In addition, each disclosure of every Japanese Unexamined Patent Application, First Publication and United States patent related to the exposure apparatus and the like recited in each of the embodiments and modified examples described above is hereby incorporated by reference in its entirety to the extent permitted by national laws and regulations.

As an example, in the above-mentioned embodiment, a description has been given of the functional film which is applied to the surface of the base material used in a state of being immersed in liquid, but the present invention is not limited thereto. The functional film of the present invention can be applied to the surfaces of various base materials other than the base material used in a state of being immersed in liquid.

Specifically, the functional film 308B according to an embodiment of the present invention is a functional film applied to the surface of the base material 308A, and includes a film of Ti-doped tetrahedral amorphous carbon (ta-C:Ti film). In the composition of the film, $\alpha$, which is defined by the following Expression (3) and which is the atomic ratio of Ti to C (Ti/C atomic ratio) is equal to or greater than 0.03 and equal to or less than 0.09.

[Expression 3]

$$\alpha = (\text{Ti/C atomic ratio}) \qquad (3)$$
$$= (\text{number of Ti atoms}) /$$
$$\{(\text{number of } sp^3\text{-C atoms}) + (\text{number of } sp^2\text{-C atoms})\}$$

here, (number of Ti atoms): number of Ti atoms occupying the film (number of $sp^3$-C atoms): number of carbon atoms having a $sp^3$ hybrid orbital occupying the film (number of $sp^2$-C atoms): number of carbon atoms having a $sp^2$ hybrid orbital occupying the film The thickness of the ta-C:Ti film can be set to be, for example, equal to or greater than 10 nm and equal to or less than 1 am. Specifically, the thickness of the ta-C:Ti film can be set to be approximately 10, 20, 30, 40, 50, 60, 70, 80, 90, 100, 200, 300, 400, 500, 600, 700, 800, 900, or 1,000 nm. Meanwhile, the thickness of the ta-C:Ti film is not limited thereto.

The functional film 308B described above has the characteristics of being chemically stable and being not likely to be contaminated, and thus can be used as not only a liquid immersion member, but also a protective film of an optical member or the like.

Further, the functional film 308B can be used as a film applied to a surface of a medical apparatus or a biomaterial. The functional film 308B has a feature of low impact on a living body and a contamination-resistant feature and therefore is widely applicable to a variety of medical apparatuses. The medical apparatus or biomaterial may be formed of Ti, Ti-based alloy, stainless steel, Ni—Ti shape memory alloy, polymer material, or ceramic material. The stainless steel may be, for example, grade 316 (SUS316, SUS316L), For example, the functional film 308B can be used as a film of metallic medical apparatuses used in a living body, such as a catheter, a guide wire, a wire mesh, an artificial heart, an endoscope, an artificial joint, an artificial bone, and a stent.

As an example, the functional film 308B can be used as a film of a stent. A stent is a medical apparatus provided inside a tubular part (for example, a blood vessel) in a living body and used to extend the tubular part. A stent is a tubular structure made from metal and having a mesh shape.

As described in the above embodiment, the functional film 308B can be formed on a base material by a FCVA method. The functional film 308B is coated uniformly even on a base material having a complicated shape and with a high adhesion force using a FCVA method. Accordingly, the functional film 308B can be coated uniformly even on a stent having a complicated shape such as a mesh shape with a high adhesion force using a FCVA method.

Specifically, a stent is provided as the base material 208A within the deposition chamber 206 of FIG. 2. A direct-current voltage is applied to the graphite target 202 within the arc plasma generation chamber 201, to thereby perform arc discharge and generate arc plasma. A negative bias voltage is applied to the stent within the deposition chamber 206. The $C^+$ ions, the $Ti^+$ ions, the $Ti^{2+}$ ions, the $Ti^{3+}$ ions, the $Ti^{4+}$ ions, and other ions which are ionized by the arc discharge are accelerated by the bias voltage, and are deposited on the stent as a dense film.

Even when a stent has a further complicated structure, the functional film 308B can be coated uniformly even on the stent with a high adhesion force. For example, even when the stent has an inner wall, the above-described ions are guided to the inner wall of the stent by the negative bias voltage applied to the stent. Therefore, the functional film 308B can be coated uniformly on the whole surface of the stent including the inner wall of the stent.

As described in the above embodiment, the functional film 308B has an antifouling property. Therefore, the functional film 308B is useful for a blood vessel stent provided in a blood vessel in use. The blood vessel stent is provided in a blood vessel in use and therefore is constantly exposed to blood to be easily contaminated. Therefore, a conventional blood vessel stent has a problem that the stent is easily degraded. On the other hand, the blood vessel stent coated by the functional film 308B has an antifouling property according to the functional film 308B. Therefore, the blood vessel stent coated by the functional film 308B is not easily degraded and, for example, can be used for a long period of time.

There is a case in which a blood vessel stent added with a medical agent elution function, which is used, for example, in a state of being coated by a medical agent, is used as a blood vessel stent. An example of the medical agent is a medical agent for preventing restenosis of the blood vessel. As described in the above embodiment, the functional film 308B is chemically inactive. When the functional film 308B is used for a blood vessel stent added with a medical agent elution function, a chemical reaction between the functional film 308B and a medical agent eluted from the blood vessel stent is prevented. That is, the functional film 308B is chemically inactive, and therefore the functional film 308B is applicable to a blood vessel stent added with a medical agent elution function. Further, in most cases, a blood vessel stent added with a medical agent elution function has a more complicated structure than a common blood vessel stent. In this regard, the functional film 308B is capable of being easily coated even on a complicated structure, and therefore the functional film 308B is capable of being easily coated even on a blood vessel stent added with a medical agent elution function.

As described above, since the functional film 308B is chemically inactive and is capable of being easily coated even on a complicated structure, the functional film 308B is useful for a blood vessel stent added with a medical agent elution function.

A medical agent coated on a blood vessel stent is not limited to a medical agent for preventing restenosis of the blood vessel. For example, a medical agent coated on a blood vessel stent may be a medical agent for preventing contamination. When the medical agent coated on a blood vessel stent is a medical agent for preventing contamination, contamination of the blood vessel stent is effectively prevented according to the antifouling property of the functional film 308B coated on the blood vessel stent in addition to the antifouling property due to the medical agent.

What is claimed is:

1. A functional film that is applied to a surface of a medical apparatus or a biomaterial, the functional film comprising a film of Ti-doped tetrahedral amorphous carbon (ta-C:Ti film), wherein:
    an atomic ratio of Ti to C in a composition of the film is equal to or greater than 0.03 and equal to or less than 0.09; and
    the atomic ratio of Ti to C is equal to a number of Ti atoms occupying the film divided by a sum of a number of carbon atoms having an $sp^3$ hybrid orbital and a number of carbon atoms having an $sp^2$ hybrid orbital occupying the film.

2. The functional film according to claim 1, wherein a static contact angle β of pure water at a surface of the film is equal to or less than 30 degrees.

3. The functional film according to claim 1, wherein a contamination index γ of a surface of the film, which is obtained through comparison with a surface of pure Ti, is equal to or less than 80%.

4. The functional film according to claim 1, wherein the medical apparatus or the biomaterial is formed of at least one selected from the group consisting of: Ti, Ti-based alloy, SUS316, Ni—Ti shape memory alloy, polymer material, and ceramic material.

5. The functional film according to claim 4, wherein:
    the medical apparatus or the biomaterial is formed of Ti;
    a proportion of carbon atoms having an $sp^3$ hybrid orbital occupying the film is equal to or less than 59%; and
    the proportion is equal to a number of carbon atoms having an $sp^3$ hybrid orbital divided by a sum of a number of carbon atoms having an $sp^a$ hybrid orbital, a number of carbon atoms having an $sp^2$ hybrid orbital, and a number of Ti atoms occupying the film.

6. The functional film according to claim 1, wherein a thickness of the film is equal to or greater than 10 nm and equal to or less than 1 μm.

7. The functional film according to claim 1, wherein the medical apparatus or the biomaterial is made from metal.

8. The functional film according to claim 1, wherein the medical apparatus is a medical apparatus used in a living body.

9. The functional film according to claim 1, wherein the medical apparatus is a stent.

10. The functional film according to claim 1, wherein the medical apparatus or the biomaterial is formed of at least one selected from the group consisting of: Ti, Ti-based alloy, SUS316, SUS316L, Ni—Ti shape memory alloy, polymer material, and ceramic material.

* * * * *